US006752927B2

United States Patent
Srinivasan et al.

(12)

(10) Patent No.: US 6,752,927 B2
(45) Date of Patent: Jun. 22, 2004

(54) SUPPRESSED CHROMATOGRAPHY AND SALT CONVERSION SYSTEM

(75) Inventors: Kannan Srinivasan, Sunnyvale, CA (US); Sheetal Saini, Fremont, CA (US); Nebojsa Avdalovic, Cupertino, CA (US)

(73) Assignee: Dionex Corporation, Sunnyvale, CA (US)

(*) Notice: Subject to any disclaimer, the term of this patent is extended or adjusted under 35 U.S.C. 154(b) by 0 days.

(21) Appl. No.: 09/797,914

(22) Filed: Mar. 1, 2001

(65) Prior Publication Data

US 2002/0162804 A1 Nov. 7, 2002

(51) Int. Cl.⁷ .................................................. C02F 1/42

(52) U.S. Cl. .................... 210/638; 210/656; 210/198.1; 436/150; 422/70; 204/632

(58) Field of Search ................................. 210/638, 656, 210/198.1; 436/150

(56) References Cited

U.S. PATENT DOCUMENTS

| | | | |
|---|---|---|---|
| 3,897,213 A | 7/1975 | Stevens et al. |
| 3,920,397 A | 11/1975 | Small et al. |
| 3,925,019 A | 12/1975 | Small Hamish et al. |
| 3,926,559 A | 12/1975 | Stevens |
| 4,265,634 A | 5/1981 | Pohl |
| 4,455,233 A | 6/1984 | Pohl et al. |
| 4,474,664 A | 10/1984 | Stevens et al. |
| 4,751,004 A | 6/1988 | Stevens et al. |
| 4,751,189 A | 6/1988 | Rocklin |
| 4,794,088 A | 12/1988 | Miyaki et al. |
| 4,861,555 A | 8/1989 | Mowery, Jr. |
| 4,999,098 A | 3/1991 | Pohl et al. |
| 5,045,204 A | 9/1991 | Dasgupta et al. |
| 5,068,090 A | 11/1991 | Connolly |
| 5,352,360 A | 10/1994 | Stillian et al. |
| 5,597,734 A | 1/1997 | Small et al. |
| 5,759,405 A | * 6/1998 | Anderson, Jr. et al. |
| 5,773,615 A | 6/1998 | Small et al. |
| 6,328,885 B1 | 12/2001 | Srinivasan et al. |
| 6,436,719 B1 | 8/2002 | Srinivasan et al. |

FOREIGN PATENT DOCUMENTS

EP    1 074 837 A1    2/2001

OTHER PUBLICATIONS

Berglund et al., "Two–Dimensional Conductometric Detection in Ion Chromatography. Postsuppressor Conversion of Eluite Acids to a Salt," *Anal. Chem.* 64:3007–3012 (1992).

Berglund, et al., "Two–Dimensional Conductometric Detection in Ion Chromatography. Postsuppressor Conversion of Eluite Acids to a Base", *Anal. Chem.* 63:2175–2183 (1991).

Yan et al., "Indirect Suppressed–Conductivity Ion Chromatography", *LCGC*, 18(2):200–204 (Feb. 2000).

(List continued on next page.)

*Primary Examiner*—Ana Fortuna
(74) *Attorney, Agent, or Firm*—Dorsey & Whitney LLP; David J. Brezner

(57) ABSTRACT

Method and apparatus for suppressed ion analysis in which a sample solution of analyte (e.g., anion) in an eluent of electrolyte counterions (e.g., sodium), is chromatographically separated. Then, the counterions are suppressed in a suppression zone and removed and used to convert the analyte ions to salt form in a salt-converting zone. The suppression and salt-converting zones may be contiguous or remote, and may be performed in devices of the membrane suppresser type. Thereafter, the salts or acids or bases formed from them (e.g., in membrane suppressor devices) are detected. Also, salt conversion can be performed using two ion exchange packed bed salt convertors in which one bed is on-line while the other is regenerated, followed by a reversal of flow.

27 Claims, 15 Drawing Sheets

OTHER PUBLICATIONS

Tanaka and Fritz, "Determination of Bicarbonate by Ion–Exclusion Chromatography with Ion–Exchange Enhancement of Conductivity Detection", *Anal. Chem.* 59:708–712 (1987).

Huang, et al., "Conductimetric detection of anions of very weak acids by incomplete suppressed ion chromatography", *J. Chromatography, A* 832:141–148 (1999).

Caliamanis et al., "Conductometric Detection of Anions of Weak Acids in Chemically Suppressed Ion Chromatography", *Anal. Chem.* 69:3272–3276 (1997).

Strong et al., "Electrodialytic Eluent Production and Gradient Generation in Ion Chromatography," *Anal. Chem.* 63:480–486 (1991).

Strong et al., "Electrodialytic Membrane Suppressor for Ion Chromatography", *Anal. Chem.* 61:939–945 (1989).

Renn et al., "Examination of the Automated Solute–Independent Calibration Technique", *Anal Chem* 61:1915–1921 (1989).

Wilson et al., "Quantitative lion Chromatography wihtout Standards b Conductivity Detection", *Anal Chem* 56:1457–1460 (1984).

Cassidy et al., "Performance of Annular Membrane and Screen–Tee Reactors for Postcolumn–Reaction Detection of Metal Ions Separated by Liquid Chromatography," *Anal Chem* 59:85–90 (1987).

Zumdahl, Steven, *Chemistry* D.C. Health and Company, pp. 44, 592–594 (1986).

Gupta et al., "Advances in Membrane Suppressors for Ion Chromatography", *J. Chromatogr. Sci.* 26:34–38 (1988).

Dasgupta, "Approaches to Ionic Chromatography", in *Ion Chromatography*, Tarter, J.G., Ed., Marcel Dekker, Inc., New York, 1987, p. 220–224.

Morris et al., "How to Make Simple High–Pressure Connections Using Polymeric Capillary Tubing", *LCGC* 10(2):149 (1992).

Tanaka and Fritz, "Separation of Aliphatic Carboxylic Acids by ion–Exclusion Chromatography Using a Weak–Acid Eluent", *J. Chromatogr.* 361:151–160 (1986).

Murayama et al., "Peak Enhancement of Carboxylic Acids in Ion–Exclusion Chromatography With Cation Exchange Hollow–Fiber Suppressor Using Neutral and Alkaline Enhancers" *J. Chromatogr.*435:417–424 (1988).

Synovec et al., Ration of Sequential Chromatograms for Quantitative Analysis and Peak Deconvolution: Application of Standard Addition Method and Process Monitoring, *Anal. Chem.* 62:1597–1603 (1990).

* cited by examiner

SUPPRESSED CHROMATOGRAPHY AND SALT CONVERSION SYSTEM

BACKGROUND OF THE INVENTION

The present invention relates to a method and apparatus using ion chromatography ("IC") in which the suppressed analyte is converted to a salt prior to detection.

Ion chromatography is a known technique for the analysis of ions which typically includes a chromatographic separation zone using an eluent containing an electrolyte, and an eluent suppression stage, followed by detection, typically performed by a conductivity detector. In the chromatographic separation stage, ions of an injected sample are eluted from a separation column. In the suppression stage, electrical conductivity of the eluent electrolyte is suppressed but not that of the separated ions. In the first generation of ion chromatography, suppression or stripping of electrolyte used an ion exchange resin bed. In an improved form of suppression, a charged membrane in the form of a fiber or sheet is used in place of the resin bed. In sheet form, the sample and eluent are passed on one side of the sheet with a flowing regenerant on the other side of the sheet. The sheet comprises an ion exchange membrane partitioning the regenerant from the effluent of chromatographic separation. The membrane passes ions of the same charge as the exchangeable ions of the membrane to convert the electrolyte of the eluent to weakly ionized form, followed by detection of the ions.

One effective form of suppressor is described in U.S. Pat. No. 4,999,098. In this apparatus, the suppressor includes at least one regenerant compartment and one chromatographic effluent compartment separated by an ion exchange membrane sheet. The sheet allows transmembrane passage of ions of the same charge as its exchangeable ions. Ion exchange screens are used in the regenerant and effluent compartments. Flow from the effluent compartment is directed to a detector, such as an electrical conductivity detector, for detecting the resolved ionic species. The screens provide ion exchange sites and serve to provide site to site transfer paths across the effluent flow channel so that suppression capacity is no longer limited by diffusion of ions from the bulk solution to the membrane. A sandwich suppressor is also disclosed including a second membrane sheet opposite to the first membrane sheet and defining a second regenerant compartment. Spaced electrodes are disclosed in communication with both regenerant chambers along the length of the suppressor. By applying an electrical potential across the electrodes, there is an increase in the suppression capacity of the device. The patent discloses a typical regenerant solution (acid or base) flowing in the regenerant flow channels and supplied from a regenerant delivery source. In a typical anion analysis system, sodium hydroxide is the eluent and sulfuric acid is the regenerant. The patent also discloses using water to replace the regenerant solution in the electrodialytic mode. In an improved form of membrane suppressor, described in U.S. Pat. No. 5,352,360, effluent from the detector is recycled through the regenerant flow channels.

In Berglund, I., et al. *Anal. Chem.* 63: 2175 (1991), another multiple detector system is described. Here, conventional IC is performed using a first conductivity detector. The effluent from that detector is passed sequentially through cation exchange and anion exchange conversion zones. For anion analysis, the effluent from the first detector is in the usual IC form of HX (wherein X is the analyte anion) as it exits from the suppressor. Two different types of convertors are disclosed. In a sequential packed column form, the effluent first passes cation (sodium) exchange resin and then anion (hydroxide) exchange resin, resulting in sequential conversion first to NaX salt and thereafter to NaOH. A permselective membrane-type convertor is also disclosed for such sequential conversion. After conversion, the ion conductivity of the sodium hydroxide is measured in the second detector and compared to the ion conductivity of the first detector. The paper states that the data reveals peaks due to very weak acids hidden in the suppressed base line or overlapped with strong acid peaks. It further states that this method allows an estimation of the pK of the analyte peak and permits approximate quantitation without standards. Problems with that system include the following: (1) incomplete conversion of the acid form analyte to NaOH due to differences in ion exchange selectivity between hydronium and sodium, and analyte anion and hydroxide on the cation and anion exchange resins respectively; and (2) analyte band dispersion in the ion exchange columns must be compensated for when ratioing the signals from the two detectors. For weak acids, for example, it can be more of a problem, because there is less free hydronium ion available to exchange for sodium ion.

In PCT Publication WO 9418555, apparatus and methods are disclosed using IC principles in which different detectors provide useful comparative signals. Specifically, in one form of the apparatus, separating means, typically in the form of a chromatographic resin column, separates the analyte ions in the presence of an eluent comprising electrolyte. The effluent from the separating means flows through suppressor means for converting the electrolyte to weakly ionized form and the analyte ions to acid or base form. The suppressed effluent flows through a first detector for detecting the conductivity of the ionic species and generates a first signal. This portion of the system is conventional suppressed IC. The effluent from the first detector flows through a salt convertor for converting the analyte ions in acid or base form and to salt form. Then, the conductivity of the salt form of the analyte is measured in a second detector means and a second signal is generated. The first and second signals are analyzed to represent a defined relationship between the output signals.

In one embodiment of WO 9418555, the analyte ions in acid or base form are converted to their corresponding salts in a single conversion with salt-forming ions of opposite charge. For example, for analyte anions represented by "X", and using $Na^+$ ion, NaX is measured in the second detector means. This is referred to herein as the "single conversion mode." It discloses a salt convertor which minimizes dispersions which could skew peak ratios of the single conversion type. One disclosed single conversion convertor is an on-line microelectrodialytic ion source which supplies the salt-forming ion through a membrane. It includes a salt-forming ion source channel, a suppressor effluent flow channel and a permselective ion exchange membrane partitioning the two channels. The membrane includes exchangeable ions of the same charge as the salt-forming ions and is resistant to transmembrane passage of the ionic species. An electrical potential is applied between the ion source channel and suppressor effluent flow channel. The latter channel is in fluid communication with the effluent from the suppressor. In operation, the signal generated in the first conductivity detector for the acid or base form of the analyte is evaluated with the signal generated in the second ion conductivity detector for the salt form of the analyte to provide extremely useful information. Other disclosed single conversion convertors include the use of an ion exchange membrane barrier without electrolysis, but with external acid or base concentrations sufficient to overcome the Donnan barrier. Still other systems include the use of a porous membrane barrier using the application of current or differential pressure to drive the acid or base salt-forming ions into the suppressor effluent flow channel. Single conversion is also disclosed by flowing the suppressor effluent stream through an ion exchange medium such as a column of an ion exchange resin bed having exchangeable ions of opposite charge to the analyte ions.

WO 9418555 also discloses a "double conversion mode" in which the analyte ions are twice-converted. In this instance, the analyte ion is converted to a salt of (a) the same type of counterion as in the single conversion mode, and (b) a common single ion of the same charge as the analyte ion by simultaneous ion exchange of the acid of base form of the analyte ions with the selected anion and cation. In one embodiment using a permselective membrane, the suppressor effluent flows in a central channel flanked by two ion source channels, one including anions and the other including cations. Permselective membranes separate the ion source channels from the suppressor effluent flow channel and include exchangeable ions of a type which permit transport of such cations and anions into the suppressor effluent flow channel to accomplish double conversion. In another simultaneous double conversion, the suppressor effluent flows from the first detector through ion exchange medium such as an ion exchange resin bed, including exchangeable anions and cations of the same type desired as in the permselective membrane. Sequential double conversion is also disclosed. In one embodiment, the suppressor effluent flows from the first detector sequentially through two ion exchange columns of opposite charge. For example, the first column includes a common, single ion of the same charge as the analyte ions so that a converted acid or base with a common anion or cation is formed in the first column which is passed to the second column for conversion to a salt, or the order of the columns may be reversed. Also, it discloses a permselective membrane system for the sequential double conversion embodiment.

Another attempt to convert suppressed chromatography effluent to a salt using a membrane suppressor in the chemical mode with countercurrent flow is disclosed in Yuan Huang, Shi-fen Mou, Ke-na Liu, *J. Chromatography*, A 832:141–148 (1999). In this approach, only enough regenerant solution was provided so that suppression was incomplete. However, it is difficult to control the background and noise. The device is extremely sensitive to both the regenerant flow rate and the eluent flow rate for a given regenerant concentration.

U.S. Pat. No. 4,455,233 discloses another approach to salt conversion, using an eluent with an acid or base with a co-ion of the same charge as the ions analyzed, in which the co-ions being in the hydronium or hydroxide form. In this approach, the electrolyte for anions is an acid and the eluent for the cation is a base. Both the eluent and the analyte are converted to salt form. Although the eluent has a lower conductivity in the salt form than the conductive form, the background in this approach can be as high as 100 US/cm. Such high backgrounds result in higher chromatographic noise. The above approach is generally not compatible with commonly used eluents for ion chromatography and require eluents that readily get converted to the salt form of lower background.

There is a need in suppressed chromatography for efficient systems to convert weakly dissociated analytes into salt form and to facilitate detection of such analytes or subsequent reaction products against a low background.

SUMMARY OF THE INVENTION

One aspect of the present invention relates to a method for suppressed ion analysis of a plurality of different analyte ions in a sample solution, each of the analyte ions being of a common charge, positive or negative. The method includes the following steps: (a) eluting the sample solution with an eluent, comprising electrolyte counterions of opposite charge to the analyte ions, through a separating medium effective to separate the analyte ions to form a separating medium effluent stream, (b) flowing the separating medium effluent stream through a suppression zone in which electrolyte counterions are removed to convert the electrolyte to weakly ionized form to form a suppressor sample effluent stream, and (c) converting the analyte ions in the suppressor sample effluent stream into salts in a salt-converting zone by reaction with salt-forming ions of opposite charge comprising the removed electrolyte counterions to form an analyte salt stream. Thereafter, the analyte salt or an acid or base formed from that product are detected.

In another aspect of the invention, the salt conversion is performed in a first packed bed salt convertor including an ion exchange medium with exchangeable cations or anions by reaction with ions of opposite charge to the analyte ions comprising to form a first analyte salt stream. At the same time, an at least partially exhausted second packed bed salt convertor is regenerated to salt-forming cations or anions. The analyte ions in the first analyte salt stream are detected. Then, flow through the first and second packed bed salt convertors is reversed so that the first one is being regenerated while a second analyte salt stream is formed in the second packed bed salt convertor. Then, the analyte ions in the second analyte salt stream are detected.

Another embodiment of the invention comprises apparatus for performing the above methods including (a) a chromatographic separator having an inlet and an outlet for separating said analyte ions in the presence of an eluent comprising electrolyte counterions of opposite charge to said analyte ions, and (b) a suppressor-salt convertor comprising a suppressor sample flow channel separated from a suppressor regenerant flow channel by a suppressor ion exchange membrane having an upstream and a downstream salt-forming zone portion, said suppressor sample flow channel having an outlet and an inlet communicating with said chromatographic separator outlet, said suppressor sample flow channel inlet and suppressor regenerant flow channel inlet being on the upstream side of each of said flow channels so that flow therethrough is in the same direction, the suppressor ion exchange membrane in the downstream salt-forming zone portion having exchangeable ions in the electrolyte counterion form serving to convert said analyte ions to salts of said electrolyte counterion.

In another apparatus according to the invention, the suppressor and salt convertor are remote from each other. The salt convertor has a regenerant flow channel inlet and analyte salt-forming flow channel inlet disposed near their upstream ends so that flow is in the same direction through both channels.

DETAILED DESCRIPTION OF THE PREFERRED EMBODIMENTS

The system of the present invention is useful for determining a large number of ionic species so long as the species to be determined are solely anions or solely cations. A suitable sample includes surface waters, and other liquids such as industrial chemical wastes, body fluids, beverages such as fruit juices and wines and drinking water. When the terms "analyte" or "analyte ions" are used herein, they include species in ionic form and components of molecules which are ionizable under the conditions of the present system.

The purpose of a conventional suppressor is to reduce the conductivity and noise of the analysis stream background while enhancing the conductivity of the analytes (i.e., increasing the signal/noise ratio) particularly for well ionized species, while maintaining chromatographic efficiency.

Figure 1:
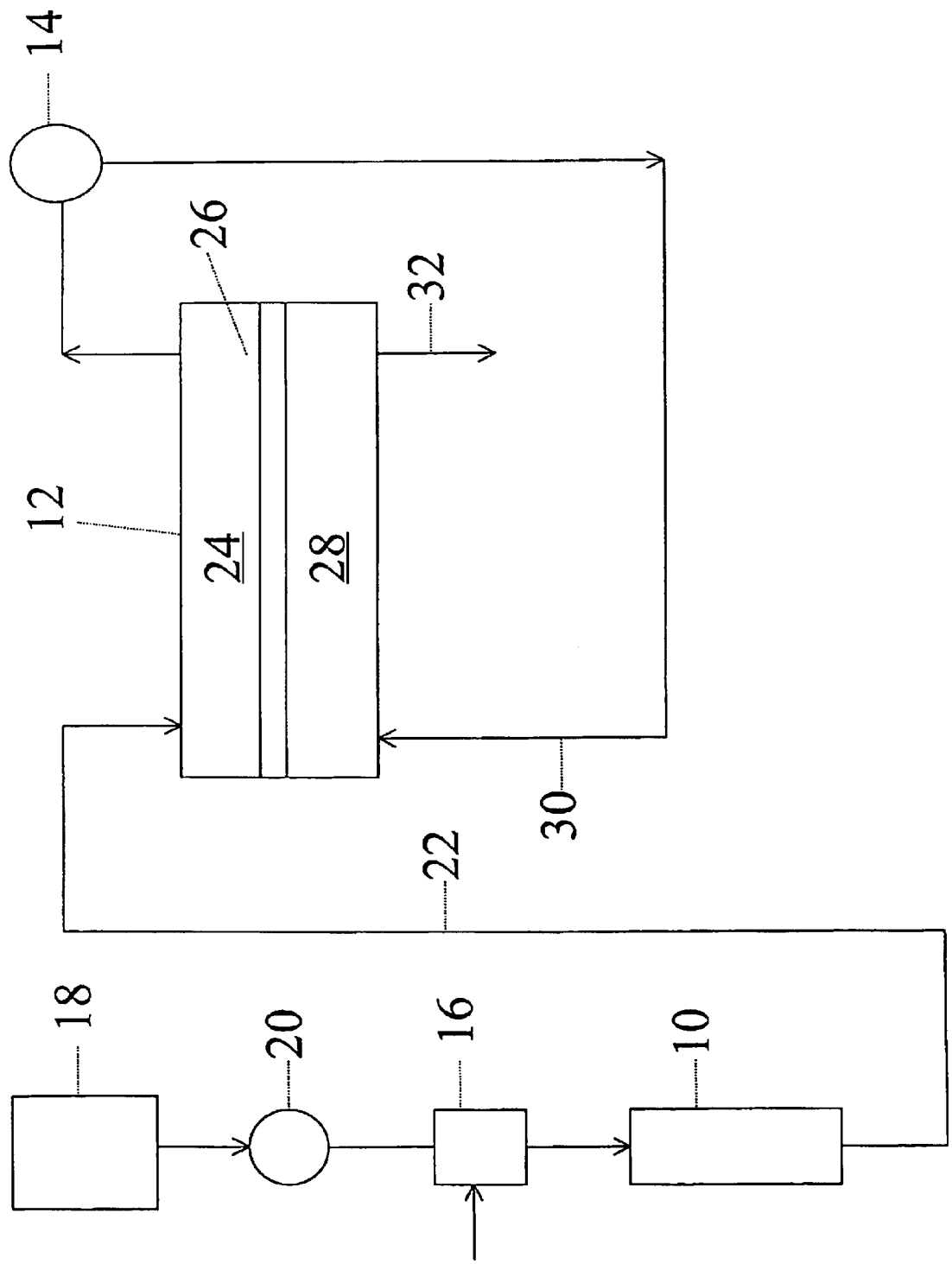
FIGS. 1–6 are schematic flow diagrams of different apparatus for performing the present invention.

Referring to FIG. 1, a simplified apparatus for performing one embodiment of the present invention is illustrated. The system includes a chromatographic separator, typically in the form of a chromatography column 10, which is packed with a chromatographic separation medium. In one embodiment, the medium is in the form of ion exchange resin. In another embodiment, the medium is a porous hydrophobic chromatographic resin as described in U.S. Pat. No. 4,265,634. Any chromatography separator can be used as is known to those skilled in the art.

Arranged in series with column 10 is a suppressor-salt convertor 12 which serves to suppress the conductivity of the electrolyte of the eluent from column 10 but not the conductivity of the separated analyte ions. In this embodiment, the analyte ions in the suppressed eluent are converted into an analyte salt stream in the downstream portion of suppressor-salt convertor 12 as described hereafter.

The effluent from suppressor-salt convertor 12 is directed to a detector, preferably in the form of a flow-through conductivity cell 14, for detecting the separated or resolved analyte ions. A suitable sample stream of analyte ions is supplied through sample injection valve 16 which is passed through the system in the solution of eluent from eluent source reservoir 18 drawn by pump 20 and then passes through sample injection valve 16. The chromatography effluent solution leaving column 10 is directed to a suppressor zone in suppressor-salt convertor 12 in which the electrolyte is converted to a weakly conducting form. In a downstream salt convertor zone of convertor 12, the analyte ions are converted to an analyte salt stream which is passed through conductivity cell 14 in which the presence of the analyte ions produces an electrical signal proportional to the amount of analyte ions. Such signal is typically directed from the cell to a conductivity meter, not shown, thus permitting detection of the concentration of separated analyte ions.

In the schematic illustration of FIG. 1, the chromatography effluent is directed in line 22 through suppressor sample flow channel 24 of suppressor-salt convertor 12 separated by suppressor ion exchange membrane 26, having exchangeable ions of opposite charge to the analyte ions, from suppressor regenerant flow channel 28. The effluent from detector 14 can be recycled in line 30 stream supplied to the inlet of flow channel 28 and out line 32 to waste. Alternatively, an independent source of regenerant (not shown) may be pumped through line 30. The streams in flow channels 24 and 28 flow concurrently (in the same direction).

The general configuration of suppressor-salt convertor 12 as illustrated in schematic form can be of the general type known in the IC field as a membrane suppressor. Any of the conventional forms of membrane suppressor may be used in accordance with the present invention such as the ones described in U.S. Pat. Nos. 4,999,098 and 5,352,360. A preferred form of membrane suppressor is illustrated in FIGS. 2–5 of those patents which illustrate an electrolytic "sandwich suppressor." Instead of only including a single membrane as schematically illustrated in FIG. 1 herein, the embodiment of FIGS. 2–5 includes a central suppressor sample channel for chromatography effluent defined on both sides by flat permselective membrane sheets. Suppressor regenerant flow channels are defined on both sides of the sandwich suppressor. As illustrated schematically in FIG. 4 of U.S. Pat. No. 5,352,360, electrodes of opposite charge are disposed to communicate, respectively, with each of the suppressor regenerant flow channels. The present description will refer to this electrolytic form of membrane device.

A suppressor of the general design sold by Dionex Corporation under the trademark ASRS suppressor can be used except that the system is set up so that all streams flow concurrently. In conventional operation of an ASRS suppressor, the regenerant stream flows countercurrent to the chromatography effluent stream ensures that the tip of the suppressor is in suppressed form so that the membrane closest to the cathode is in the hydronium form. The electrolyte counterion (sodium) is predominantly drawn across the membrane in the upstream half of the device which is in cation form. Thus, the downstream portion of the analyte stream is substantially in the hydronium ion form.

Figure 2:
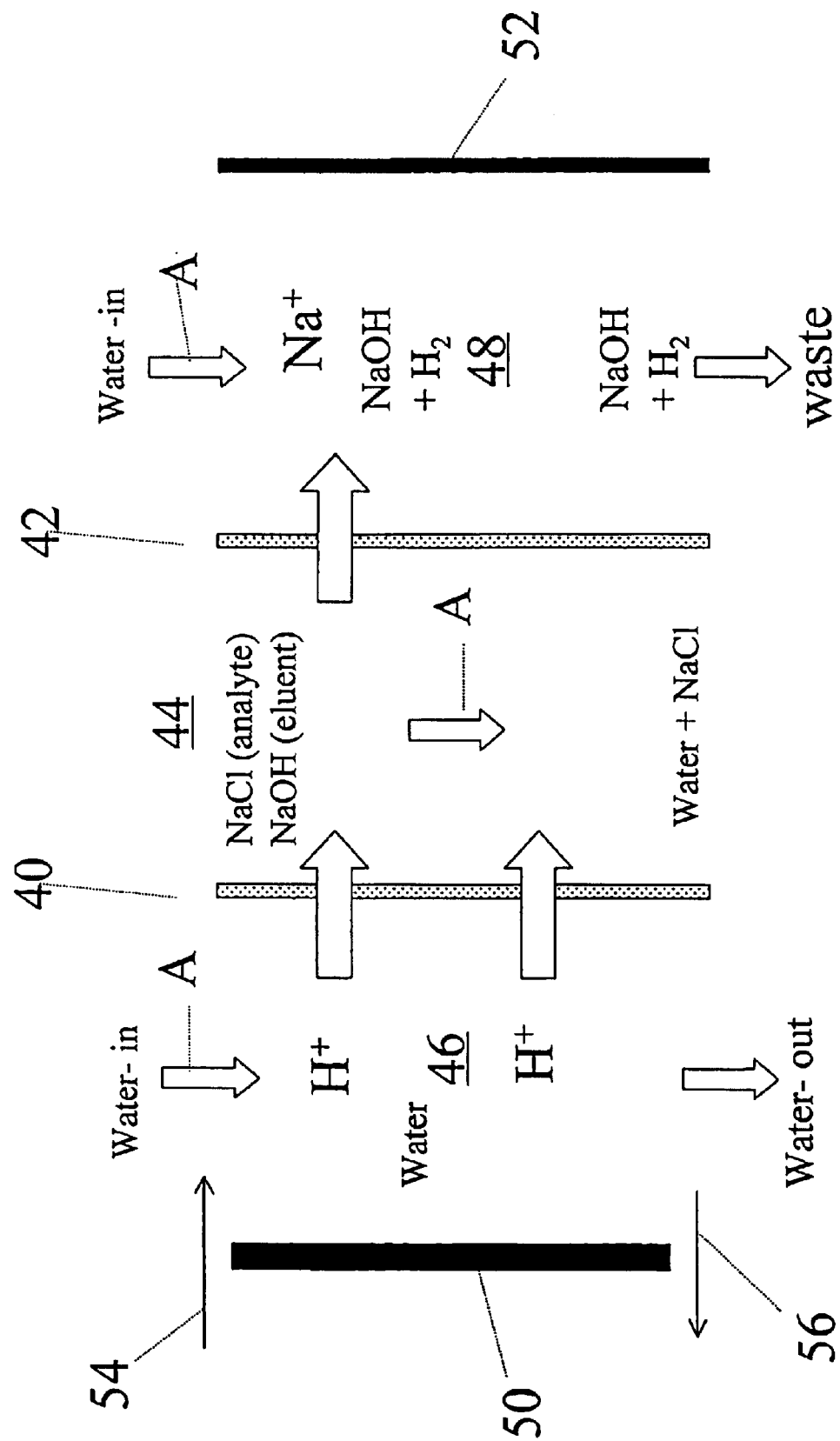

FIG. 2 is a schematic view illustrating the reactions which occur in one embodiment of suppressor-salt convertor 12 of FIG. 1 used for the analysis of analyte anions. The suppressor of FIG. 2 includes two permselective ion exchange membranes 40 and 42 defining therebetween a central suppressor sample channel 44. Outside of membranes 40 and 42 are suppressor regenerant flow channels 46 and 48 contained within the interior walls by a suppressor not shown but illustrated in detail in the above patents. Electrodes in the form of anode 50 and cathode 52 communicate with the outer walls of channels 46 and 48, respectively. Ion exchange medium, preferably in the form of ion exchange screens (not shown), are preferably included in channels 44, 46 and 48 and form a bridge between the electrodes on the outside of the channels and membranes 40 and 42 and between membranes 40 and 42 in the central channel.

Figure 3:
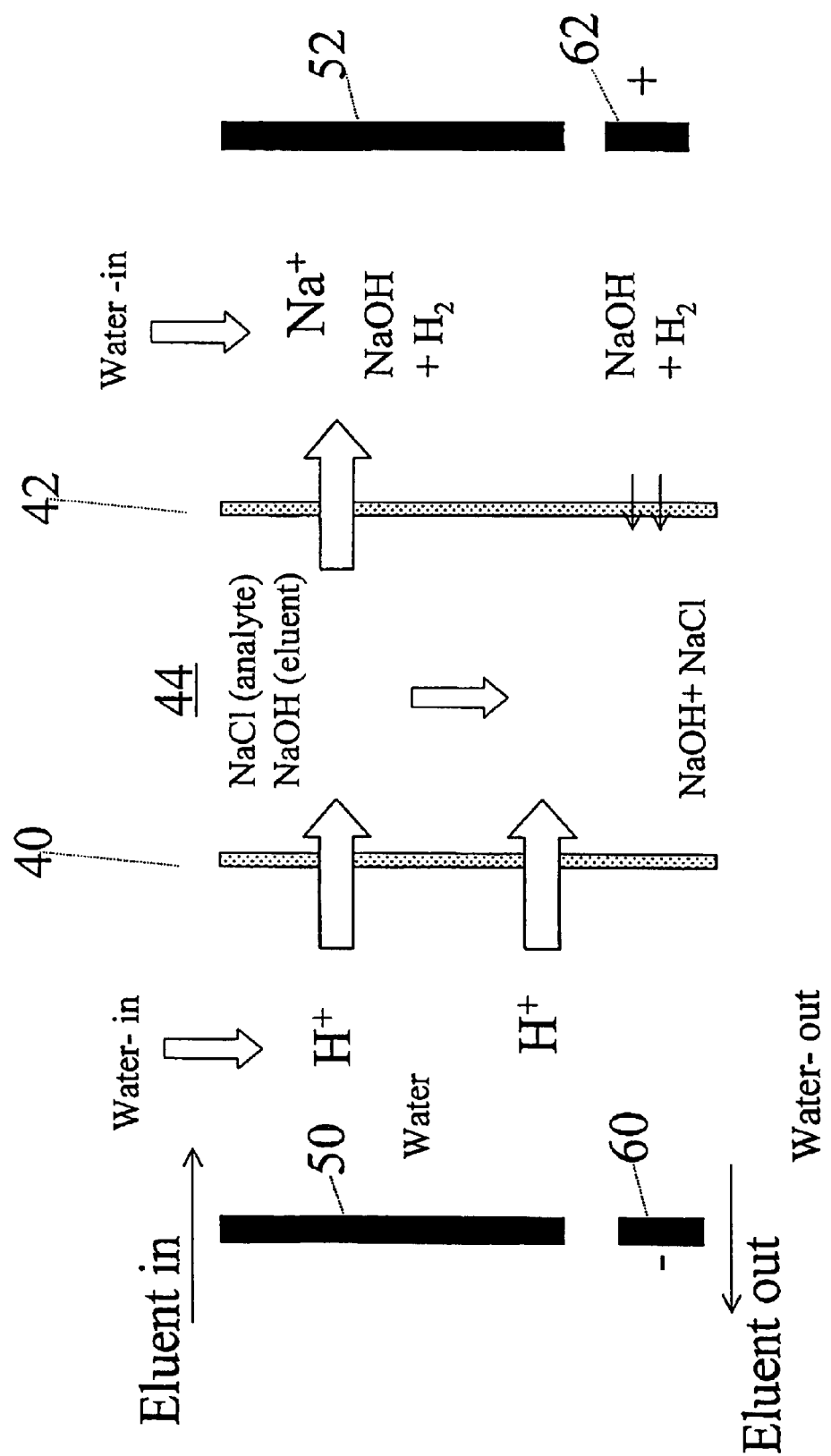
Figure 4:
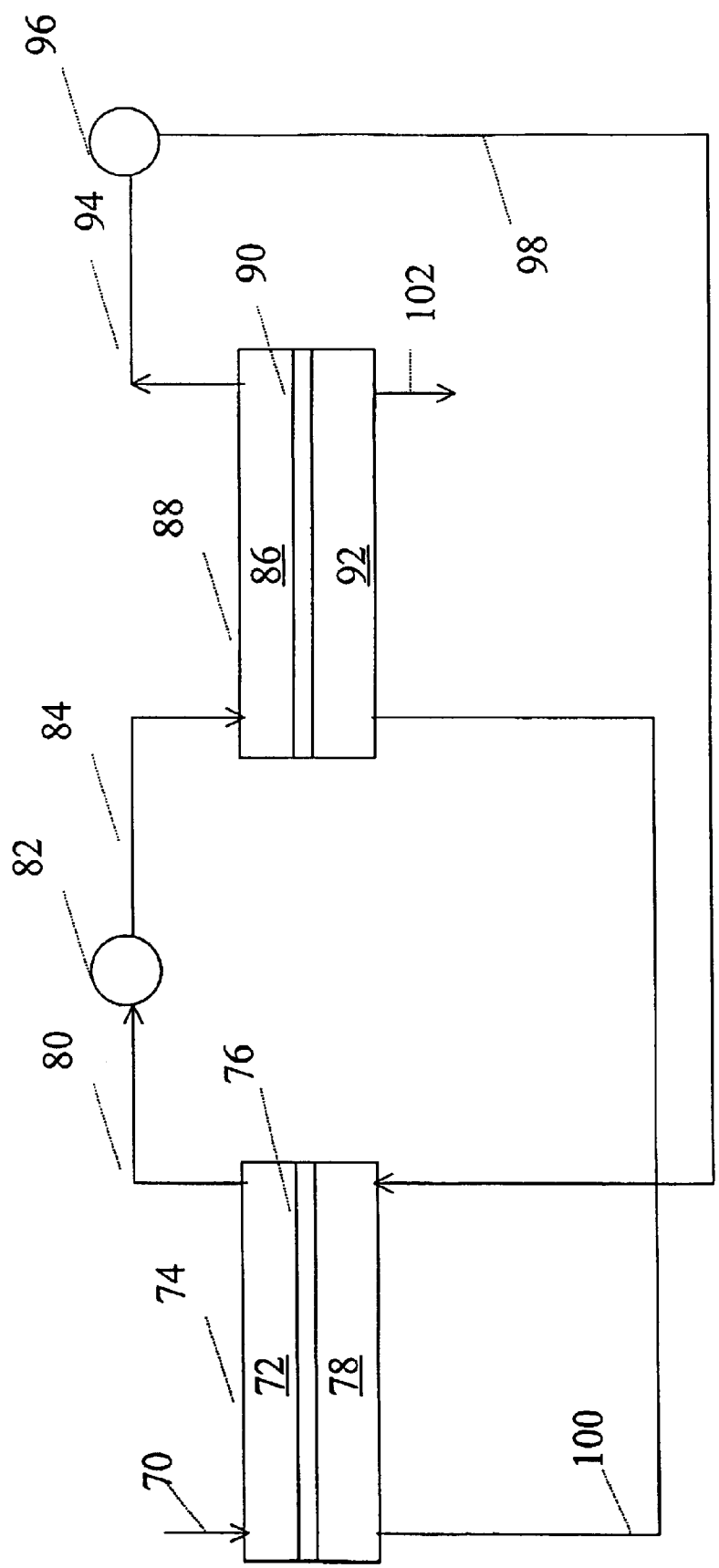

Effluent from chromatography column 12 flows through inlet 54 into channel 44, and out outlet 56 isolated from flow channels 46 and 48 by membranes 40 and 42 as illustrated in FIGS. 3 and 4 of U.S. Pat. No. 5,352,360. In this embodiment, water is supplied as the regenerant stream in regenerant channels 46 and 48 flowing in the direction of arrow A. First the upstream or suppression zone of suppressor-salt convertor 12 will be described. Water is electrolyzed in channel 46 to provide hydronium ion which passes through membrane 40. Assuming sodium hydroxide electrolyte used during chromatography, the electrolyte counterion is sodium which passes through membrane 42 under the influence of cathode 52. Hydroxide is converted to water in the chromatography effluent flowing through central channel 44 also in direction A. In the negatively charged suppressor flow channel 48, the sodium ion is converted to sodium hydroxide.

The suppression zone reactions and conditions are substantially the same as the reactions that take place in the aforementioned U.S. Pat. No. 5,352,360. A feature of this embodiment which distinguishes from that patent is that the analyte ions flowing in the suppression one sample eluent stream channel 44 are converted into a salt in a salt-forming zone by reaction with salt-forming ions of opposite charge. Such salt-forming ions comprise electrolyte counterions (e.g., sodium) removed during suppression. As illustrated in FIG. 2, the salt-forming zone is coextensive with the outlet end of membranes 42 includes exchangeable ions in sodium form which supply the ions to convert the analyte to an analyte salt stream. Conditions in the salt-forming zone are selected so that suppression is substantially complete (the same degree of suppression as in a conventional suppressor with an ASRS suppressor) in the inlet or upstream portion of the suppressor. Sufficient electrolyte counterion is present at the downstream or exit end of the membrane 42 to permit conversion of the analyte ions to a salt form (e.g., NaA) wherein "A" represents analyte ion and "Na" is a representative counterion of the electrolyte. In the embodiment of FIG. 1, suppressor-convertor 12 is an electrolytic sandwich configuration with concurrent flow of the chromatography effluent in channel 44 and the regenerant in channels 46 and 48 to effectuate substantially complete suppression in the upstream or suppression zone while simultaneously converting the analyte to salt form in the downstream or salt-forming zone at the outlet of the suppressor.

One way to facilitate salt formation using concurrent streams in a conventional ASRS suppressor is to flow the suppressor effluent through the longer chamber of the ASRS device. This can be accomplished by reversing the polarity of the electrodes as illustrated schematically in FIG. 2. Regenerant flow is also reversed and is concurrent with the eluent flow. At the inlet in the device, the eluent ions are drawn towards the cathode and replaced by the hydronium ions from the anode. The function of suppression is still maintained by the flux of hydronium ions and sodium ions through the ion exchange membranes. Since the exit end of the device is continuously flushed with suppressed effluent, these ion exchange sites are in the electrolyte counterion (sodium) form. Reversal of polarity causes the regenerant stream, into which the electrolyte counterions are transmitted through the membrane 42, to flow through a longer flow channel 48. The net effect of reversing the polarity is to ensure that the outlet end of suppressor-salt convertor 12 is in the salt form and available for converting the suppressed analytes to the salt form.

Alternatively, the electrode length can be shortened at the downstream or outlet end without changing the polarity of the device. Specifically, for example, the electrode length can be adjusted to extend extensively with about 30–90% of the upstream or inlet portions of the membranes bounding the central flow channel 44 of the device, preferably about 40% to 60% and most preferably about 50%. In this way, the desired degree of conversion to a salt can be controlled because of a lack of potential being applied in part or all of the salt convertor zone.

While conversion to the salt form may result in a lower response for fully dissociated species, the conversion to the salt form for weakly dissociated species results in an improved linearity and, depending upon the small pKa, an improved response.

The degree of conversion to a salt form is dependent on the pKa and concentration of the analytes. The analyte has to be in the ionized form for good conversion. The extent of conversion can be monitored by comparing the peak response in the suppressed mode versus the salt formation mode. For strongly ionized species, the conversion to the salt form results in a decline in response when compared to the suppressed mode. The extent of conversion can be calculated from the expected conductivity response for a given analyte concentration which in turn can be calculated from the equivalent conductance and concentration of the individual ions. For weakly dissociated species, the conversion to the salt form results in improved linearity of response with concentration. If excellent linearity of response is observed for a weakly ionized species over a wide range of concentration (for example, 0–50 ppm), then constant conversion of the analytes to the salt form can be inferred in that concentration range. A smaller range of linearity implies constant conversion in the range where linearity was observed and lesser conversion in the non-linear regime. It is also possible to calculate the extent of conversion by calculating the anticipated response for a given concentration. The condition to accomplish substantially complete suppression in the suppressor zone and salt conversion in the salt form would be apparent to those skilled in the art. Under typical operation conditions, salt conversion can be accomplished with at least about 10% of the outlet or downstream length of the membrane 42 exchangeable ions predominantly in the electrolyte counterion form, more preferably 30% to 90% and most preferably 40% to 60%. One suitable test for monitoring salt conversion is by plotting a response versus concentration curve for the detected analytes. A linear response for weakly dissociated species implies constant conversion. The length of the outlet or downstream length can be adjusted to allow for complete conversion in a desired range of concentration. The extent of ionization of some weakly dissociated species can be controlled by the extent of leakage across the membrane and this is done by adjusting the length of the outlet or downstream length.

The degree of conversion to a salt is the salt-forming zone can be measured, e.g., by ion chromatography of the electrolyte counterion after salt formation. Suitably, at least about 10% conversion takes place, preferably at least about 40–60%, and more preferably at least about 80% to as high as about 95–100%.

In another alternative of the integral suppressor-ion convertor 12 of FIGS. 1 and 2, not shown, the outlet end of membranes 40 and 42 may be formed of material which has exchangeable ions of opposite polarity. For example, for anion analysis, the exit end of membranes 40 and 42 may be in the form of exchangeable cations. Similar spacial relations to the foregoing discussion of the shortening of the electrode length apply. The principle is that the system is adjusted to ensure that the outlet or downstream end of the membrane in the salt-forming zone is in the electrolyte counterion form.

Another embodiment of the integral suppressor-ion convertor 12 is illustrated in FIG. 3. The outlet ends of membranes 40 and 42 are maintained in electrolyte counterion form by the use of short electrodes of opposite polarity to anode 50 and cathode 52. Like parts will be designated by like numbers in FIGS. 2 and 3. As illustrated, for anion analysis, cathode 60 is disposed at the outlet end or downstream of anode 50 and an anode 62 is disposed at the outlet end or downstream of cathode 52. The relative length of the upstream electrodes for suppression and downstream electrodes for salt conversion can be adjusted depending upon the desired degree of conversion to the salt form while maintaining full conversion to the suppressed form in the upstream suppression portion of the suppressor. Typically, the upstream electrode is at least as long as the downstream electrode, preferably the ratio is at least 1:0.4, more preferably at least 1:0.2 or higher. Alternatively, the applied potential can be varied to adjust the degree of salt conversion.

The system of FIGS. 1–3 has been described with respect to the analysis of anions. It is also applicable to the analysis of cations with an appropriate modification of the device to reverse polarity. Thus, the cathode and anode are reversed, the exchangeable ions of the suppressor ion exchange membrane are switched to the anion form rather than the cation form, and the electrolyte counterions are anionic, such as MSA, as is conventional in cation chromatography.

Referring to FIG. 4, another embodiment of the invention is illustrated in which suppression and salt conversion are performed in separate communicating devices. In other words, the salt-forming communicates with but is remote from the suppression device. Referring to FIG. 4, the sample effluent from chromatography (line 22 in FIG. 1) flows in line 70 into the suppressor sample flow channel 72 of suppressor 74 separated by a suppressor ion exchange membrane 76 from suppressor regenerant flow channel 78. For anion analysis, suppressor 74 can be a conventional electrolytic suppressor of the type sold under the ASRS trademark by Dionex Corporation with countercurrent flow. (A second set of downstream electrodes as described above may be used.) The suppressed chromatography effluent flows out line 80 into optional first detector 82 for detection of the suppressed resolved sample as a conventional chromatography.

The effluent from detector 82 flows through line 84 into the salt convertor regenerant flow channel 86 of salt convertor 88 separated by salt convertor ion exchange membrane 90 from the salt convertor regenerant flow channel 92. As with the salt-forming zone of FIGS. 1–3, flow in channels 86 and 92 is concurrent. Membrane 90 has exchangeable ions of the same charge as the electrolyte counterions. The function of salt convertor 88 is the same as the function of the salt-forming zone in the integral suppressor-salt convertor 12 of FIG. 1. Similar principles apply for accomplishing salt conversion. One difference is that salt conversion is independent of suppression because they are accomplished in different devices. One advantage of this system is that it can be operated continuously with no external regenerant solution. Since in this system suppression is accomplished in the first device, both the suppressed and the salt form of the analytes can be monitored using independent detectors.

The effluent from flow channel 86 flows through line 94 into a second detector 96 which detects the analyte ions in salt form as described for FIG. 1. The effluent from detector 96 flows through line 98 and serves as the regenerant stream for suppressor regenerant flow channel 78. The effluent from channel 78 flows in line 100 to the inlet of salt convertor regenerant flow channel 92. The effluent from flow channel 92 flows to waste through line 102. In this system, no external regenerant stream is required for either suppressor 74 or salt convertor 88.

In another embodiment, the suppressor of WO 99/44054 could be used as the suppressor in a system using a remote salt convertor so that the suppressor effluent is the source of salt-forming ions.

Figure 5:
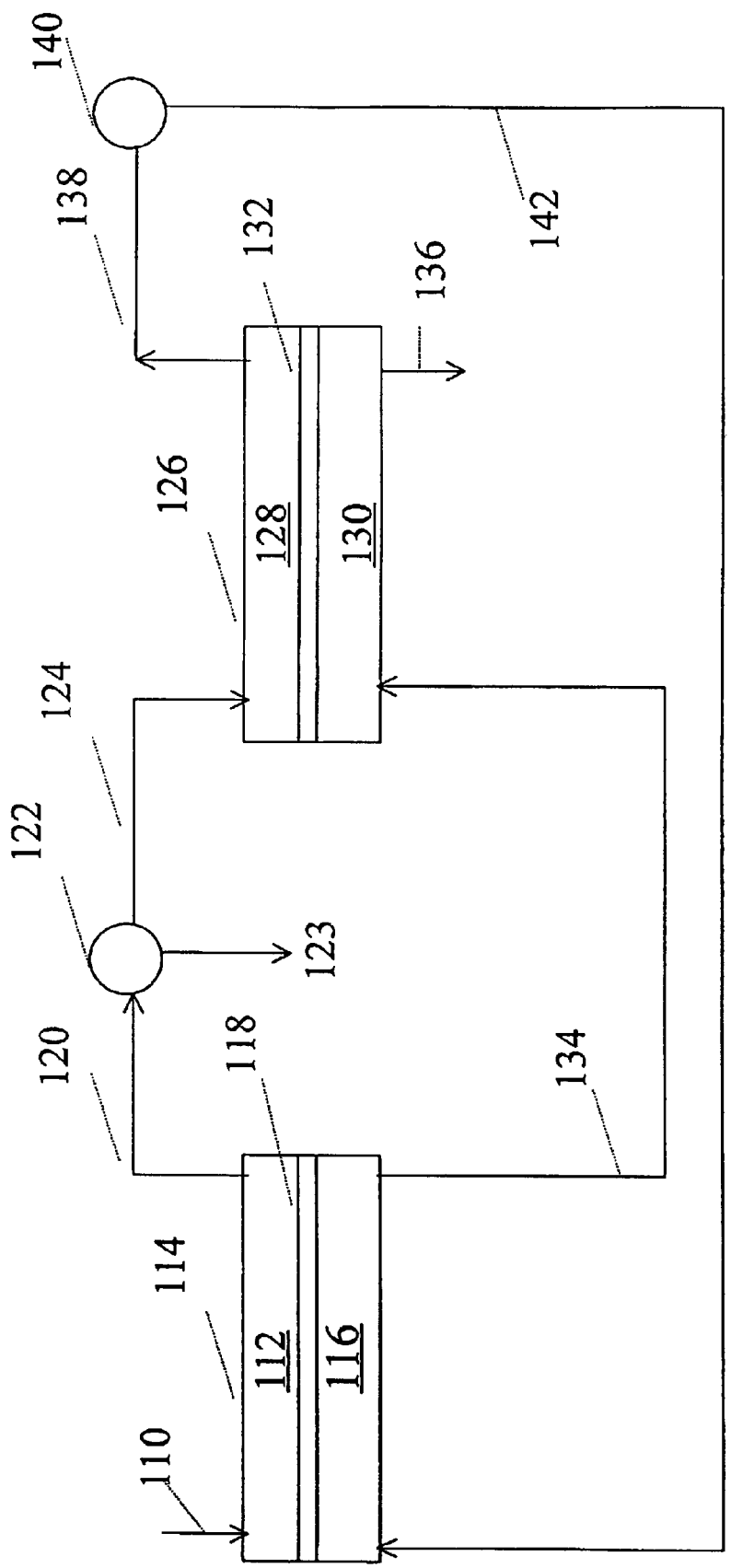

In another embodiment, illustrated in FIG. 5, the analyte ions are first converted to salt form and optionally detected, as described above. Thereafter, the analyte salt is converted to an acid or base of the electrolyte counterions for improved conductivity during detection. By way of example, if "A" generally designates an analyte anion and "M" designates the electrolyte counterion used in the salt convertor, the analyte ion is converted to MA. In the acid or base convertor, MA is converted to the base MOH. Thus, in the second stage detection the electrolyte counterions are detected in hydroxide form, an indirect measure of the analyte ions in the sample. In one embodiment, the acid or base convertor uses an ion exchange membrane with exchangeable ions of opposite charge to the ion exchange membrane in the salt convertor. Alternatively, a packed bed acid or base convertor may be employed.

For cation analysis, a typical eluent is MSA, and the analyte ion (e.g., $Na^+$) is converted to sodium MSA form by a salt convertor either in integral form with the suppressor as in FIG. 1 or in a remote unit as in FIG. 4. Thereafter, the NaMSA is converted to the HMSA acid form by passing through an anion suppressor such as the ASRS® suppressor sold by Dionex Corporation operated in a recycle mode.

FIG. 5 illustrates one embodiment of the sequence of salt conversion followed by acid or base conversion. Suppressed chromatography effluent in line 110 is directed into the analyte flow channel 112 of salt convertor 114 separated from salt convertor regenerant flow channel 116 by salt convertor ion exchange membrane 118. (In an alternate embodiment, not shown, the operation of salt convertor 114 can be the same as that of salt convertor 88 in FIG. 4 and so the description of that embodiment will be incorporated by reference.) The sample effluent converted to an analyte salt in flow channel 112 flows through line 120 into detector 122 which detects the analyte salt in the stream. The analyte in 120 may be detected in detector 122 with part of it optionally flowing to waste in line 123.

Effluent from detector 122 flows in line 124 into an acid or base convertor 126 wherein the analyte salt of the electrolyte counterion is converted into an acid or base of that counterion for subsequent detection. A suitable non-electrolytic acid or base convertor is of the type sold by Dionex Corporation under the trademark AMMSIII. As illustrated, the analyte salt in the form of MSA flows into acid or base convertor flow channel 128 which is separated from acid or base flow channel 130 by ion exchange membrane 132 having exchangeable ions of opposite charge to membrane 118 and thus of the same charge as the analyte cation. In the analysis of cations, analyte cations are exchanged for hydronium ions to form the acid of the electrolyte counterion and the electrolyte counterion M is converted to the MOH for hydroxide form. The effluent from channel 116 flows in line 134 to the inlet side of flow channel 130 serving as the aqueous solution for continuously regenerating acid or base convertor 126. The effluent from channel 130 flows to waste in line 136. The acid or base channel 128 flows in line 138 to detector 140 and where the acid or base is detected. The effluent from detector 140 flows in line 142 and serves as the ion source in channel 116 for salt convertor 114. In an alternative embodiment, not shown, salt conversion may be accomplished in integral suppressor-salt convertor as illustrated in FIG. 1 followed by conversion to an acid or base in the manner described in FIG. 5.

One advantage of the above acid or base conversion system illustrated for cation analysis is that the acid formed may be more conductive than the suppressed base form for both highly dissociated and partially dissociated analyte ions. For example, consider sodium and ammonium as the analytes. Under normal suppression, the sodium and ammonium with counterions are converted to sodium hydroxide and ammonium hydroxide. The conversion to a salt in the salt convertor results in lower sensitivity for sodium because, for example, in the NaMSA form, MSA ion have a lower equivalent conductance than hydroxide ion. For ammonium, this conversion may result in improvement and sensitivity (depending on its concentration). Thus, the salt form for fully dissociated species has a lower response than the suppressed form. On reconverting the analyte to the MSA acid form, the MSA form becomes more conductive than both the salt and the suppressed form. This is due to the fact that hydronium ion is more conductive than hydroxide ion. Thus, improved sensitivity for all cations may be achieved in this double conversion.

Figure 6:
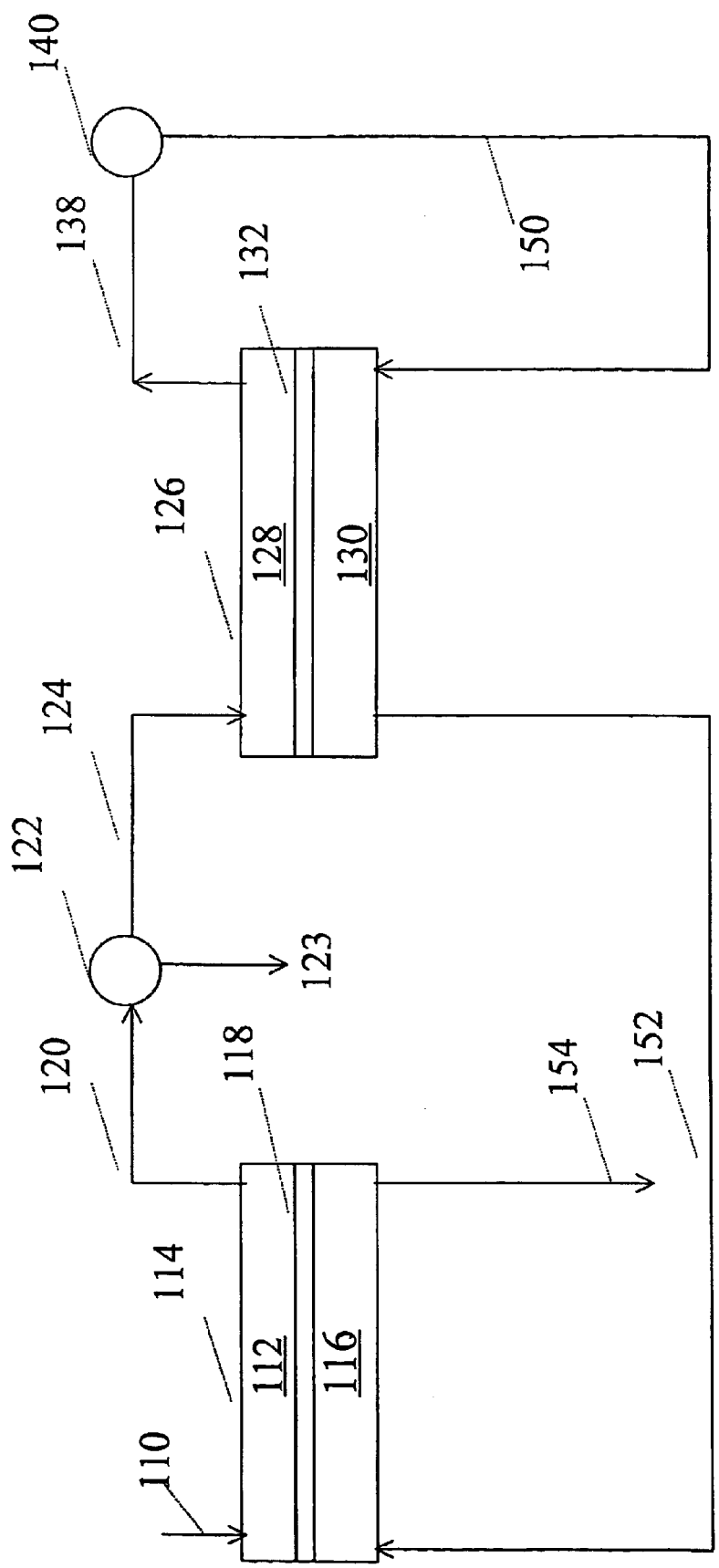

In another embodiment, combining a salt convertor and an acid or base convertor similar to the system of FIG. 5, is illustrated in FIG. 6. In this instance, an acid or base convertor using an electrolytic suppressor of the type sold by Dionex Corporation under the trademark ASRS is used for analysis of cations instead of the non-electrolytic acid or base convertor 126 described with respect to FIG. 5. Referring to FIG. 6, salt convertor 114 is of the same type as salt convertor 114 in FIG. 5 except for the source of regenerant solution. The inlet sample stream 110 is of the same type as in FIG. 5. Like parts will be designated like numbers for FIGS. 5 and 6. In distinction to FIG. 5, in FIG. 6 the effluent from detector 140 flows through line 150 and recycles to acid or base convertor 126 serving as the regenerant liquid source in channel 130 which flows countercurrently to the analyte salt flowing in channel 128. The effluent from channel 130 flows in line 152 to the inlet side of channel 116 in salt convertor 114. The effluent from channel 116 flows to waste in line 154. The flow systems of FIGS. 5 and 6 are different ways of accomplishing the same functions. First, conversion to salt and then to an acid or base.

In another embodiment, not shown, the packed bed suppressor of WO 99/44054 could be used as the acid or base convertor.

Figure 14:
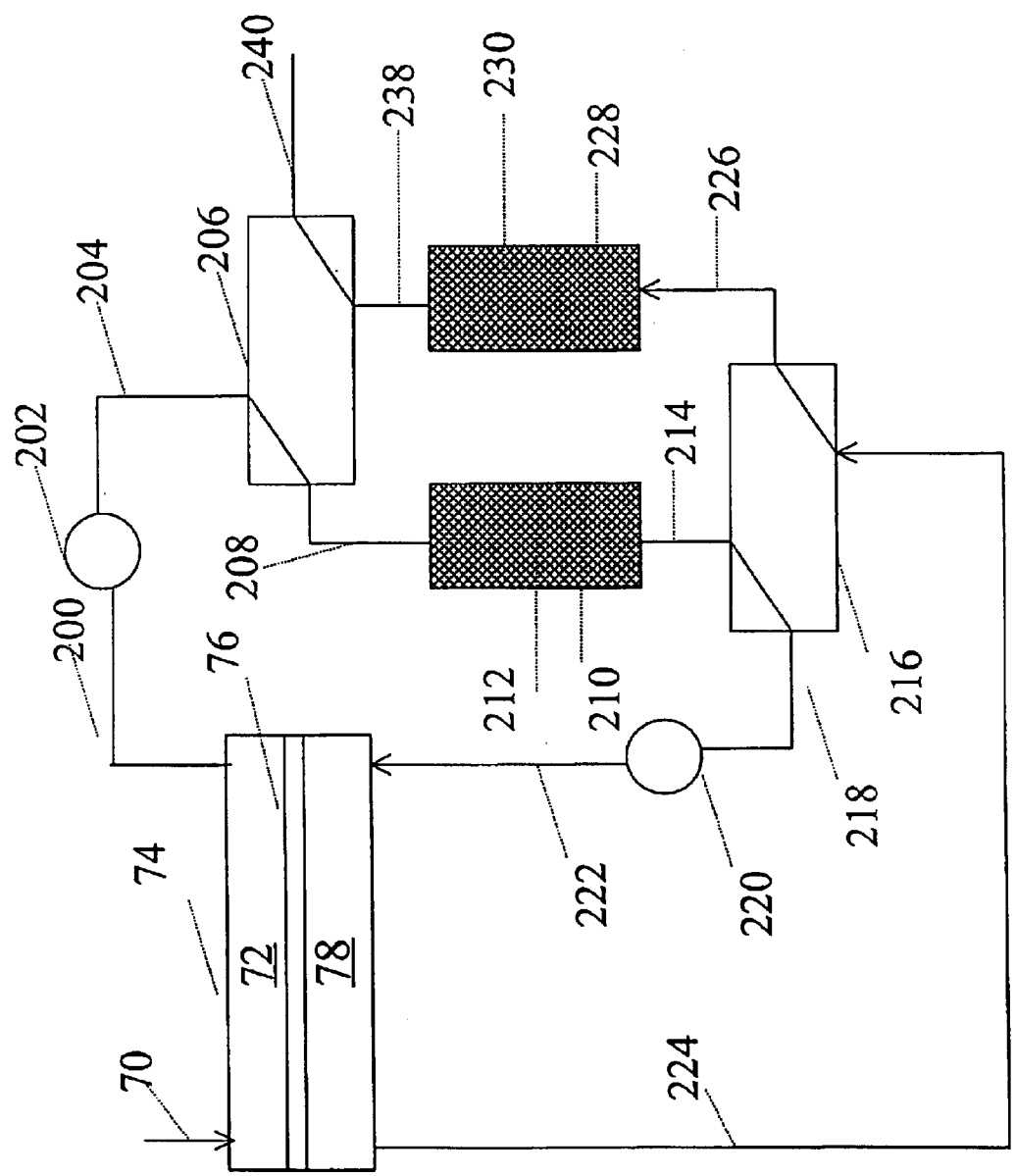
FIGS. 14 and 15 are schematic flow diagrams of different apparatus according to the present invention using packed bed salt convertors.

In another embodiment of the present invention illustrated in FIG. 14, a packed bed form of salt convertor is illustrated in place of the membrane device salt convertors described above. As used herein, the term "packed bed" refers to the packed bed of the type described in U.S. Pat. No. 5,773,615 or alternative flow-through ion exchange materials such as disclosed in Example 7 of that patent. In the embodiment of FIG. 14, two packed bed devices are used in which one packed bed device is regenerated while the other one is used for salt conversion. Upon exhaustion of the packed bed device in use, the valve is switched to regenerate the exhausted suppressor while using the other regenerated packed bed device. The system of FIG. 14 using the electrolyte counterion as a source of regenerant could also be used with a single packed bed but this would require downtime or regeneration so it is less desirable than the continuous system of FIG. 14.

Referring to FIG. 14, the chromatography portion of the system can be the same as that described above with respect to FIG. 1 through chromatography column 10 and line 22. (Alternatively, the suppressor could be one or two packed bed suppressors such as described in U.S. Pat. No. 5,597, 334.) Thus, this portion of the system will not be described. The effluent from the chromatography column flows in line 70 to the suppressor sample flow channel 72 of suppressor 74 separated by suppressor ion exchange membrane 76 from suppressor regenerant flow channel 78. Since the suppressor of FIG. 14 can be of the same type of the suppressor of FIG. 4 as described above, like numbers will be used to designate like parts in these two suppressors. The effluent from flow channel 72 flows through line 200 into conductivity cell 202 of the type described above. In the illustrated dual salt convertor embodiment, the effluent from detector 202 flows in line 204 to valve 206 and exits valve 206 in line 208 which flows into the first packed bed salt convertor 210 containing ion exchange material such as a packed bed of ion exchange resin 212 with exchangeable ion of opposite charge to the analyte ions. In convertor 210, the analyte ions are converted into a salt form of the electrolyte counterion in an analogous but reversed way to suppression as described in U.S. Pat. No. 5,773,615. Salt conversion in a packed bed is also described in WO 9418555.

The principles in converting the acid or base form of the analyte into a salt are the same as those described above in that the acid or base form of the analyte is converted to the electrolyte counterion salt of the analyte. As in conventional suppression, the electrolyte counterion is in weakly ionized form in line 200 with the analyte ion typically an acid or base form which can be detected as in conventional chromatography by conductivity detector 202. The salt converted analyte exiting convertor 210 flows in line 214 to a second valve 216 and from there in line 218 to a second conductivity cell 220 in which the analyte in salt form is detected. The effluent from conductivity detector 220 flows in line 222 to the inlet side of the regenerant flow channel 78 of suppressor 74. As described above, flow in channels 72 and 78 are countercurrent as in a conventional suppressor. The effluent from suppressor regenerant flow channel flows in line 224 back to valve 216 and into line 226 into the bottom of the second salt convertor 228 containing a packed bed of resin particles 230 as illustrated. The effluent stream from the regenerant flow channel 78 includes electrolyte counterions which have migrated across ion exchange membrane 76 according to the well known principles of membrane suppression. During salt conversion in packed bed 230, the electrolyte counterions are depleted and replaced by hydronium ions or hydroxide ions. Thereafter, packed bed 230 is regenerated by flowing the electrolyte counterions in line 224 through line 226 into packed bed 230 to convert the exchangeable ions of the ion exchange resin back into electrolyte counterion form. From there, the regenerant stream flows in line 232 back through valve 206 and to waste in line 240. The depleted packed bed used for salt conversion may be available in the hydronium or hydroxide form and may be used for the conventional suppression mode. This automatically converts the packed bed to the eluent counteranion or cation form.

When on-line salt convertor 210 is exhausted, valves 206 and 216 are switched to reverse the flow of the analyte and regenerant streams flowing through convertors 210 and 228. With the valving switched, convertor 210 is regenerated and convertor 230 is on-line with the analyte serving to convert the analyte to the salt. In this way, the system is used continuously with one packed bed salt convertor being used to convert the analyte to salt while the other one is being regenerated followed by valve switching for use of the other suppressor on-line for salt conversion while the first one is regenerated. This system can be used continuously with the electrolyte counterion which migrates across suppressor ion exchange membrane 76 being used as the regenerant for the packed bed salt convertor.

Figure 15:
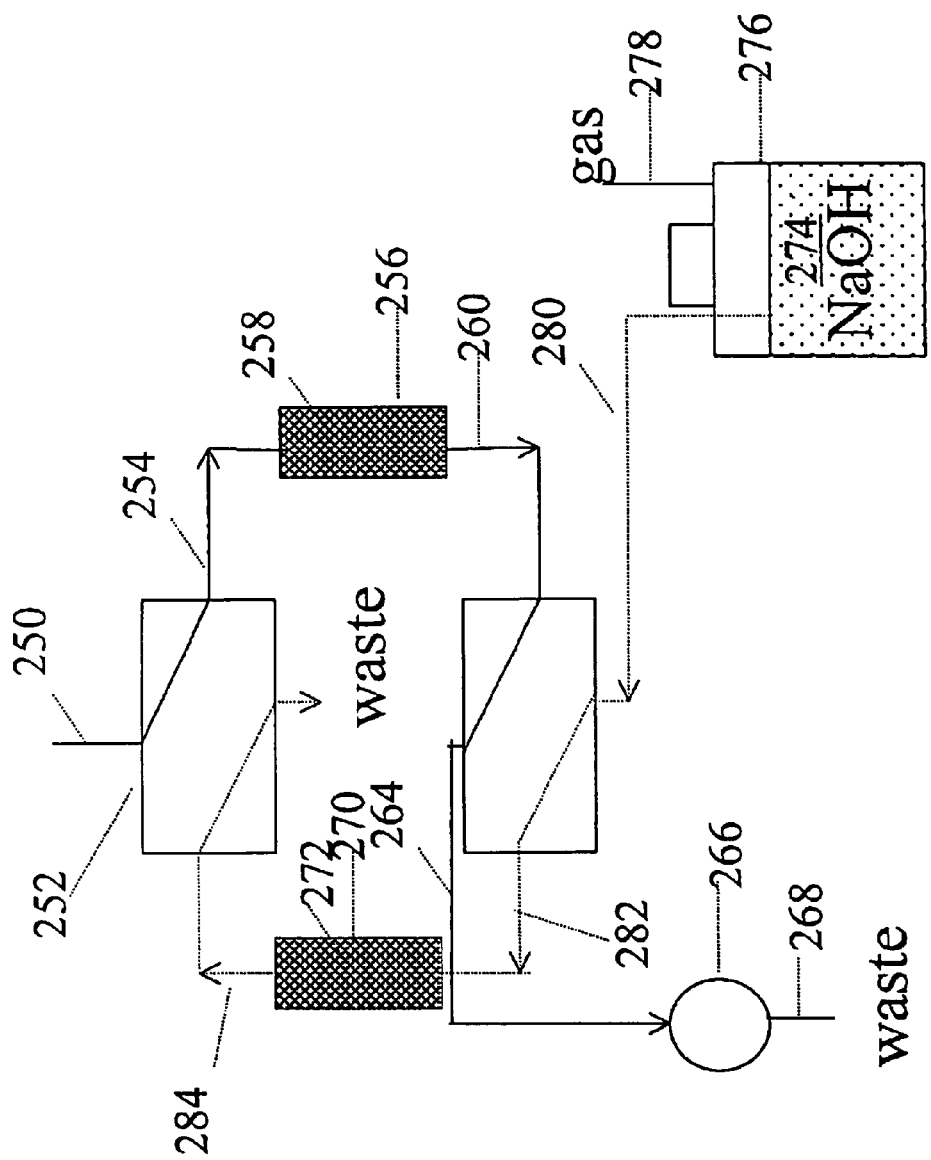

In another embodiment illustrated in FIG. 15, a system is illustrated for using two packed beds in which a first one is used on-line for salt conversion while the second one is regenerated followed by a switching of the valve so that the second salt convertor is on-line while the first one is regenerated. This is the same as FIG. 14. However, in FIG. 15, an external source of regenerant solution, typically in the form of an acid or base such as the electrolyte used for the eluent, can be used for regeneration. In that regard, a valving system can be used similar to that set forth in U.S. Pat. No. 5,773,615 which describes an alternate suppression and regeneration of two packed bed suppressors followed by reversal of flow for continuous operation.

Referring to FIG. 15, one embodiment of a continuous system for suppression and regeneration using two packed beds and an external regenerant reservoir is illustrated. A stream of chromatographically separated and suppressed analyte from a conventional suppressed ion chromatography system flows into the system in line 250 into valve 252 and from there through line 254 into first packed bed salt convertor 256 containing a packed bed of ion exchange particles 258 typically in the form of the electrolyte counterion. When using a sodium hydroxide electrolyte in the chromatography effluent, the ion exchange resin may be in the form of the electrolyte counterion or sodium. Alternatively, the electrolyte counterion may be in any form of the same charge as the electrolyte counterion such as other alkali metal salts such as lithium, cesium, or potassium. From bed 256, the analyte salt stream flows in line 260 to valve 262 and from there to a detector in the form of conductivity cell 266 and then through line 268 to waste.

Simultaneous with salt conversion in salt convertor 256, salt convertor 270 containing ion exchange packed bed 272 is regenerated. In the illustrated embodiment, a solution of electrolyte counterion or other ions suitable for salt conversion 274 is contained in reservoir 276. A suitable pump such as pressurized gas in line 278 forces an electrolyte counterion in a liquid stream to flow through line 280 into valve 260. From there, the liquid flows in line 282 into the bottom of packed bed 272 and flows therethrough to regenerant exhausted exchangeable ions such as in the hydronium or hydroxide form into the form of the electrolyte counterion. The effluent stream from packed bed 270 flows through line 284 back through valve 252 and from there through line 286 to waste.

The system is used with the illustrated valve setting while packed bed 256 contains sufficient electrolyte counterions to convert the analyte in line 254 to analyte salt in line 260.

When the exchangeable ions in packed bed 258 are exhausted so that the analyte ions are not effectively converted to salt form, valves 252 and 260 are reversed. In this instance, the electrolyte source from reservoir 276 flows upwardly through bed 258 to convert the exchangeable ions to electrolyte counterion form while convertor 270 is on-line converting analyte ion to analyte salt form. In this manner, flow through the two packed beds is reversed so that one is used for salt conversion while the other one is regenerated followed by a reversal of the valving resulting in continuous operation of the system. In one alternate system, not shown, the suppressors can be in the packed bed form rather than membrane suppressors.

With packed bed devices, the capacity of the bed can be calculated and based on the analyte concentrations an estimate of the regeneration time can be easily derived. The membrane and packed bed devices of the present invention may be operated continuously or discontinuously as described above. All publications referred to in this specification are incorporated herein by reference.

As set forth above, for simplicity, substantial portions of the present specification and many claims refer to two channel ion exchange membrane devices for suppression, salt conversion and/or acid or base conversion. One flow channel of the described membrane devices contain the sample stream and the other contains a stream that interacts with the sample stream by supplying or receiving ions ("the interacting flow channel"). Such claims are intended to encompass both a two channel membrane device and a three channel device containing two membranes as described above with respect to the suppressor membrane device of FIGS. 2–5 in U.S. Pat. No. 5,352,360 as schematically illustrated in FIGS. 2 and 3 herein. Thus, for example, when the claims refer to a first electrode communicating with a sample flow channel, this encompasses direct communication (as by direct contact of the first electrode with the sample flow channel), or indirect communication (as by direct contact of the first electrode with the third flow channel adjacent to the second membrane separating the sample flow channel from the third flow channel in the sandwich membrane device), in which the first electrode is of opposite charge to the second electrode communicating (typically directly) with the interacting flow channel.

To illustrate the present invention, the following examples of its practice are provided.

EXAMPLE 1

Figure 7:
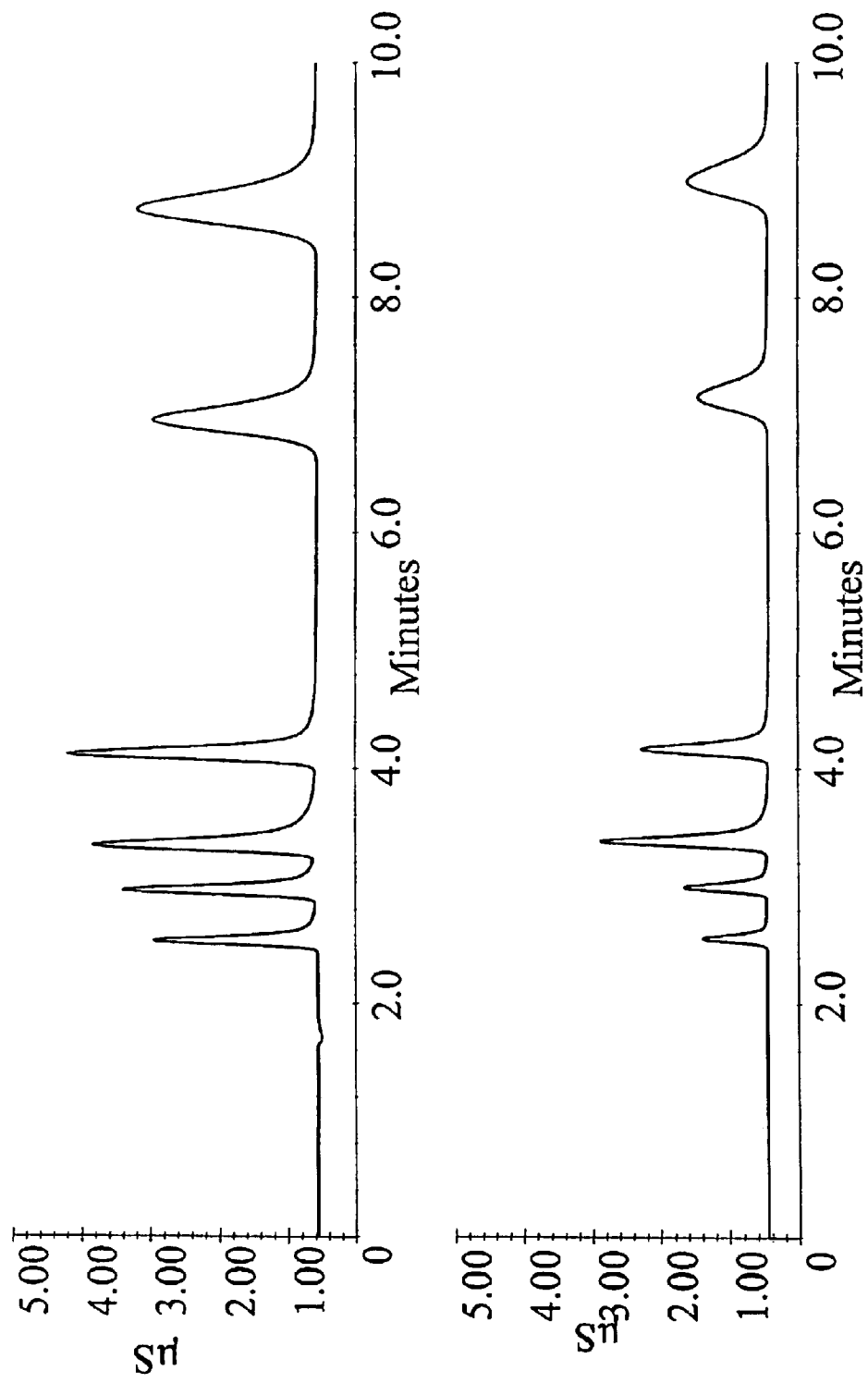
FIGS. 7 and 9–12 are comparative chromatograms comparing use of systems according to the present invention and the prior art.

This example illustrates the operation of the system of FIG. 1. A Dionex Corporation DX500 system was used for this testing with a Dionex CS12a column and 20 mN MSA eluent. A commercially available Dionex CSRS ultra suppressor was used as the suppressor device and operated in the recycle mode of operation. The analytes comprised of a mixture of lithium, sodium, ammonium, potassium, calcium and magnesium. The CSRS ultra suppressor was first operated at 100 mA in the normal mode of operation. The regenerant flow was then switched to the concurrent flow mode (or reversed flow mode) as per the current invention and the device was powered at 100 mA. The chromatograms were compared as shown in FIG. 7. The sensitivity for all the peaks were lower in the salt form, however, ammonia showed a higher relative response than the other ions in the salt form for this concentration.

EXAMPLE 2

This example compares to operation of a conventional suppressor and suppression-salt conversion as in FIG. 1. The efficiencies between the normal and the reverse flow mode were compared in this example and is shown in the following Table 1. The results indicated superior performance of the reversed mode of operation, which is another benefit of converting the analytes to the salt form.

TABLE 1

COMPARISON OF EFFICIENCY-NORMAL vs. REVERSE MODE

| | Normal Efficiency | Reversed Efficiency |
| --- | --- | --- |
| Lithium | 5146 | 6751 |
| Sodium | 6033 | 7132 |
| Ammonium | 4567 | 6367 |
| Potassium | 6908 | 7464 |
| Magnesium | 3958 | 4531 |
| Calcium | 4220 | 4750 |

EXAMPLE 3

Figure 8:
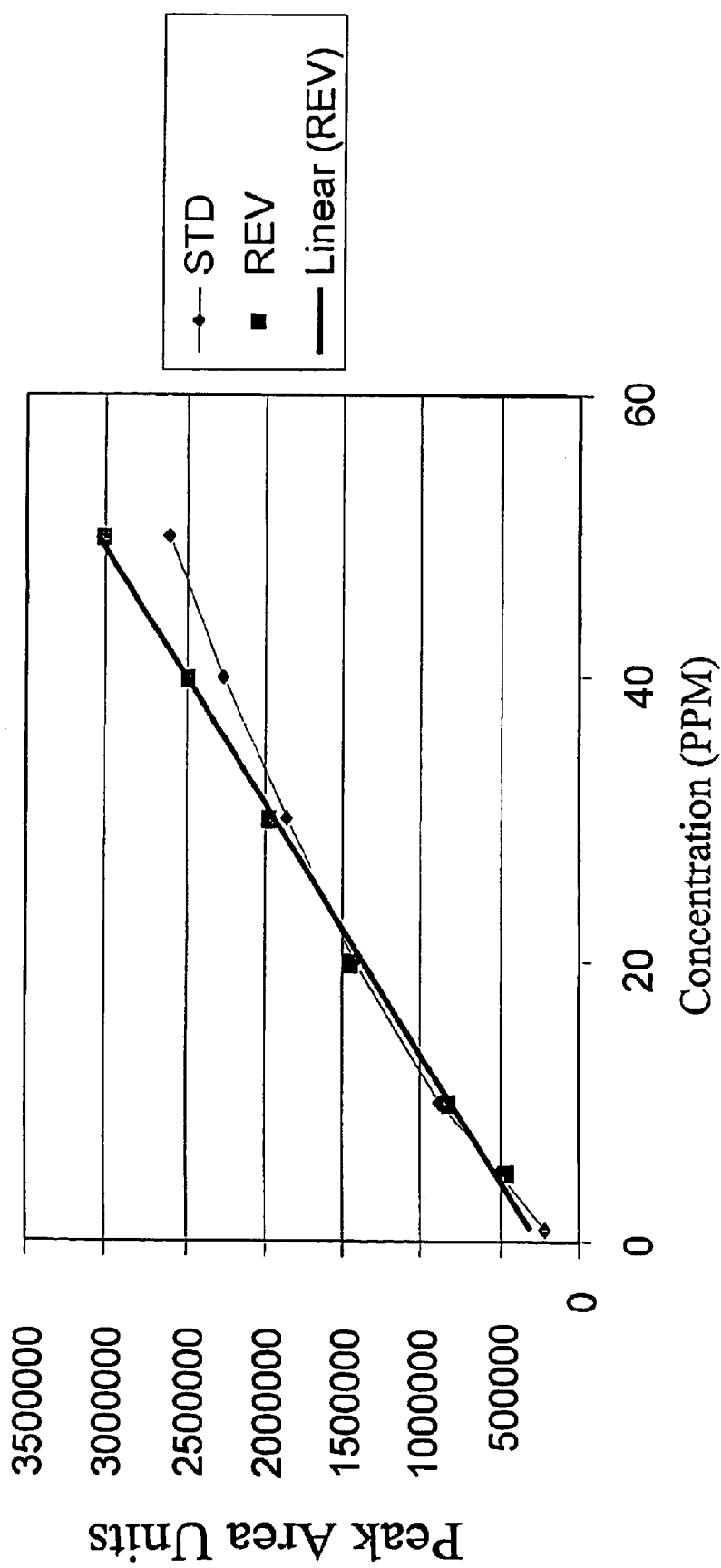
FIGS. 8 and 13 are diagrams of response curves using the present invention.

Response versus concentration curves were generated by monitoring the response for the ions in the normal and the reverse mode of operation for a range of concentration up to 50 ppm. All other conditions were similar to Example 1. The results are plotted for ammonia in FIG. 8 and indicates linear response up to 50 ppm for the reverse mode of operation. The normal mode of operation showed poor linearity. The correlation coefficient for linearity for the reverse mode was 0.997 indicating linear response and complete dissociation of the ions in the salt form. The correlation coefficient for linearity for the reversed mode was 0.997 indicating linear response and constant conversion to the salt form. In comparison to the above result, the normal mode showed non-linear behavior particularly when the concentration of ammonia increased. This can lead to quantitation errors. This example shows the method of the present invention has excellent linearity leading to improved quantitation.

EXAMPLE 4

Figure 9:
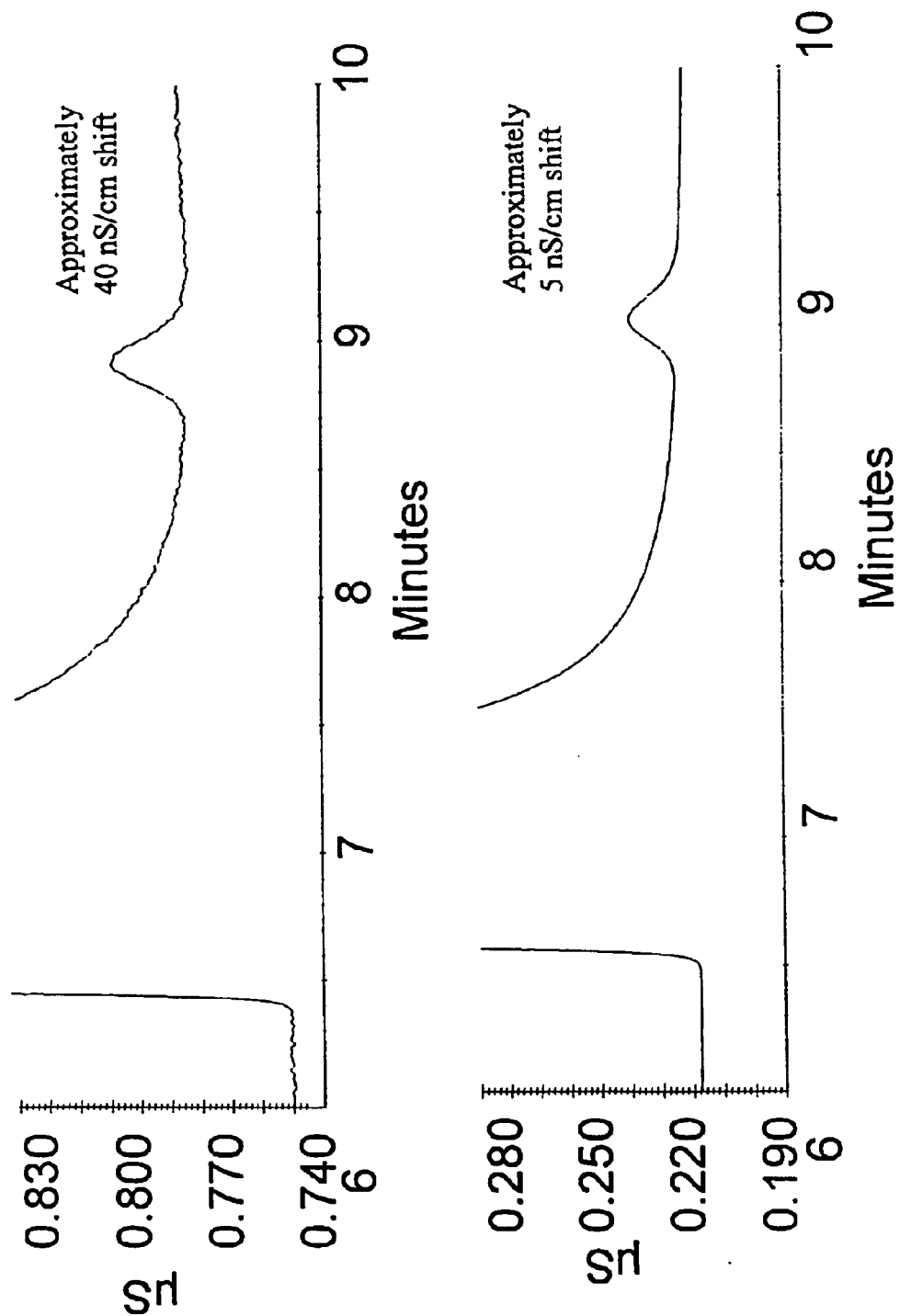

In this example, 10 ppb of ammonia was injected in the presence of 1000 ppm of sodium and the suppressor was operated both in the normal and the reversed mode of operation. All other conditions were similar to Example 1. The results as shown in FIG. 9 indicated a lower shift in the baseline for the reversed mode of operation. Roughly, 40 nS/cm shift was observed due to the high level of sodium in the sample stream for the normal mode of operation. The reversed mode showed a much lower baseline shift of roughly 5 nS/cm indicating superior performance for this application. The noise was also lower in the reversed mode indicating that the sensitivity would be higher for this application in the reversed mode of operation.

EXAMPLE 5

Figure 10:
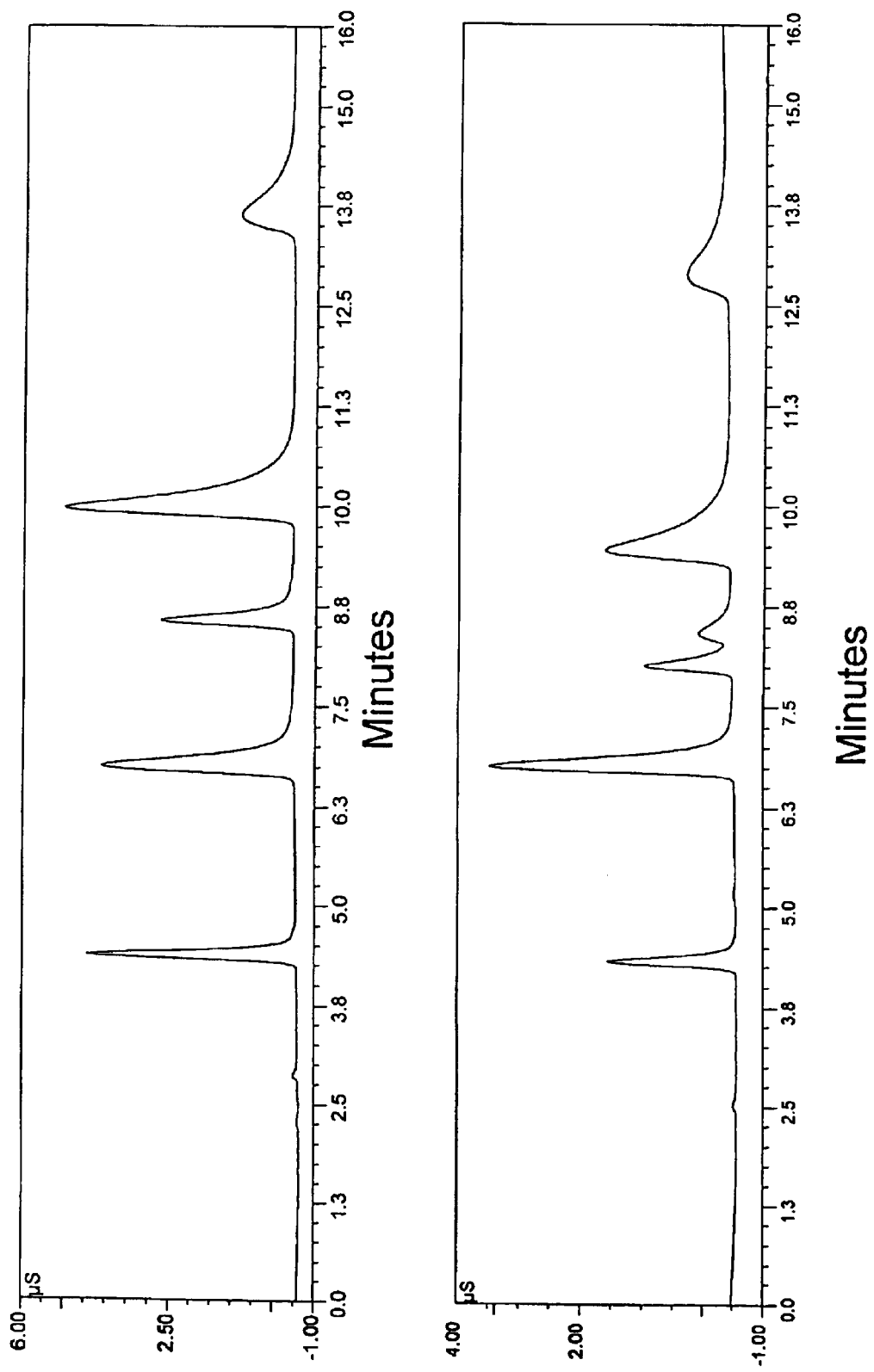

This example shows the operation of the system of FIG. 1. A Dionex Corporation DX500 system was fitted with an AS 11column and a gradient separation was attempted for a mixture of anions in both the normal and the reversed mode of operation. The analytes comprised of Bromate, Azide, Selinite, Sulfate and Phthalate ions. The gradient conditions were 0.5 mM to 30 mM NaOH for the first 16 minutes of operation and then up to 25 minutes at 30 mM NaOH for 1 ml/min. The suppressor was operated in the reversed mode of operation and the polarity was reversed to ensure that the tip of the suppressor was in the salt form. The results as shown in FIG. 10 indicated higher relative response for the weak acids in the salt form. Carbonate was poorly detected in the normal mode of operation and was detected with high sensitivity in the reversed mode of operation again demonstrating superior performance of the devices of the present invention.

EXAMPLE 6

Figure 11:
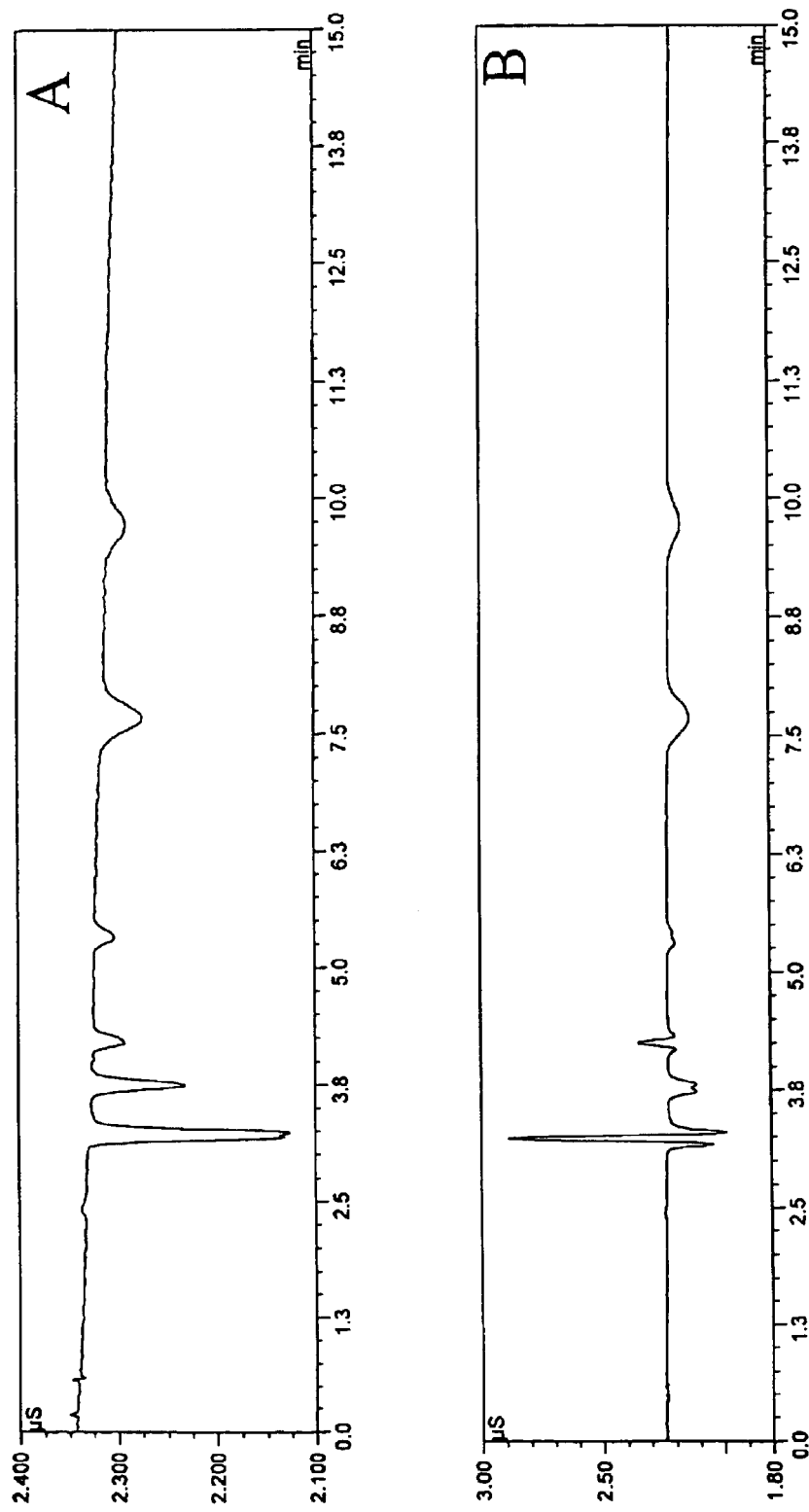

A Dionex Corporation DX500 system was used for this testing with a Dionex CS12a column and 20 mN MSA eluent. A modified version of the 4 mm Dionex CSRS ultra suppressor was used as the suppressor device. The modification consisted of reducing the length of the anode to about 75% of the channel length. The net result of this change was a higher level of leakage of the regenerant across the suppressor as evident by the higher background. The suppressor was operated at 100 mA with the regenerant flow switched to the concurrent flow mode (or reversed flow mode) as per the current invention and the device was powered at 100 mA. The device produced negative peaks for an injection of 250-ppb concentration for a mixture of cations as shown in FIG. 11a. The device when injected with 750-ppb showed a mixture of both positive and negative peaks making integration difficult (FIG. 11b).

EXAMPLE 7

Figure 12:
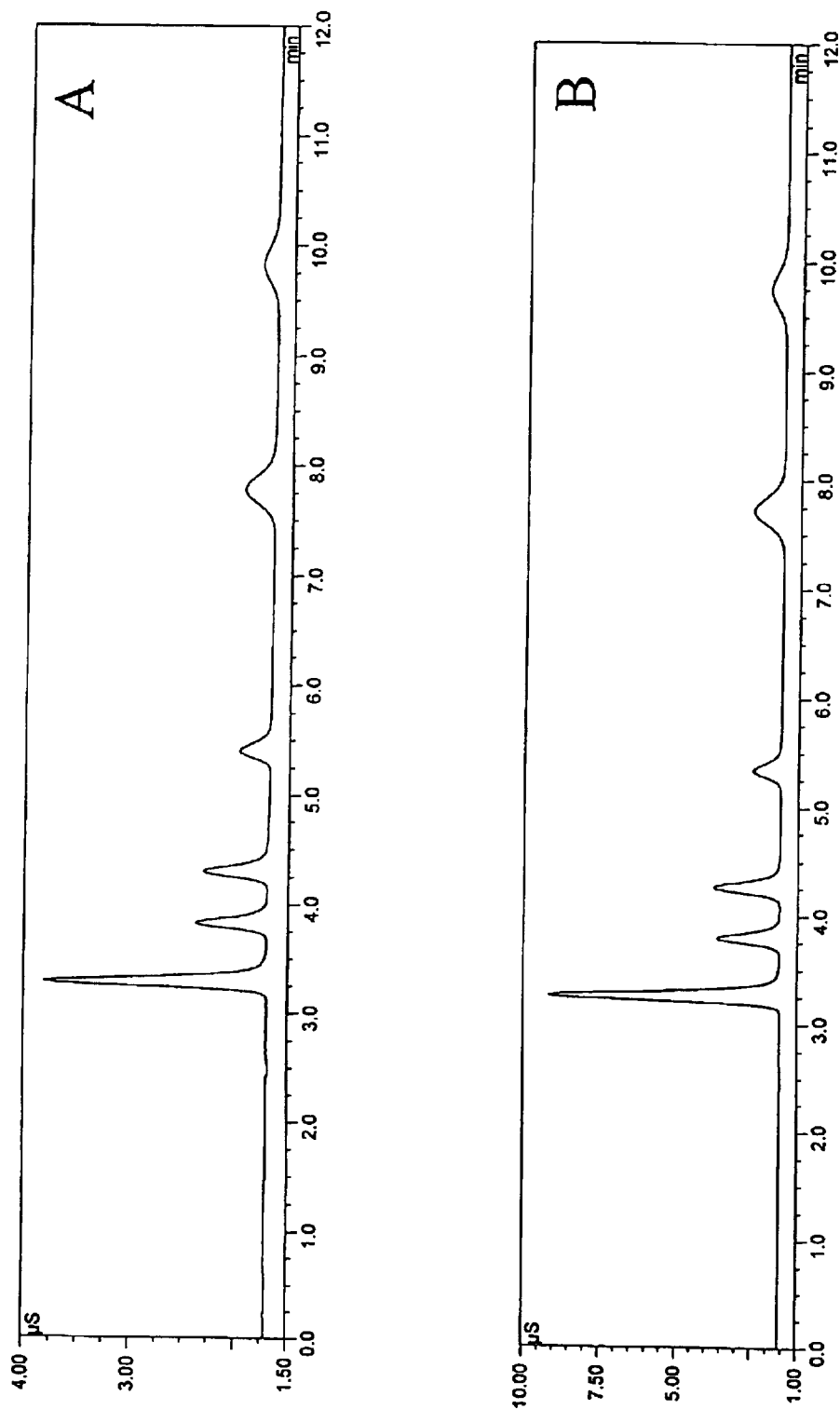

The experimental setup was similar to Example 6 with the exception that an additional 2 mm AMMS device was used for converting the cation analytes to acid form. This setup is shown in FIG. 5. The regenerant waste is diverted from the first suppressor to the AMMS suppressor in this mode. Thus, continuous conversion of the analytes to the eluent form is accomplished. The device is injected with the same samples from Example 6. Positive peaks with high sensitivity were observed as MSA and is shown in FIGS. 12a and 12b. The peak response in this mode was (area and height) higher than the salt form.

EXAMPLE 8

Figure 13:
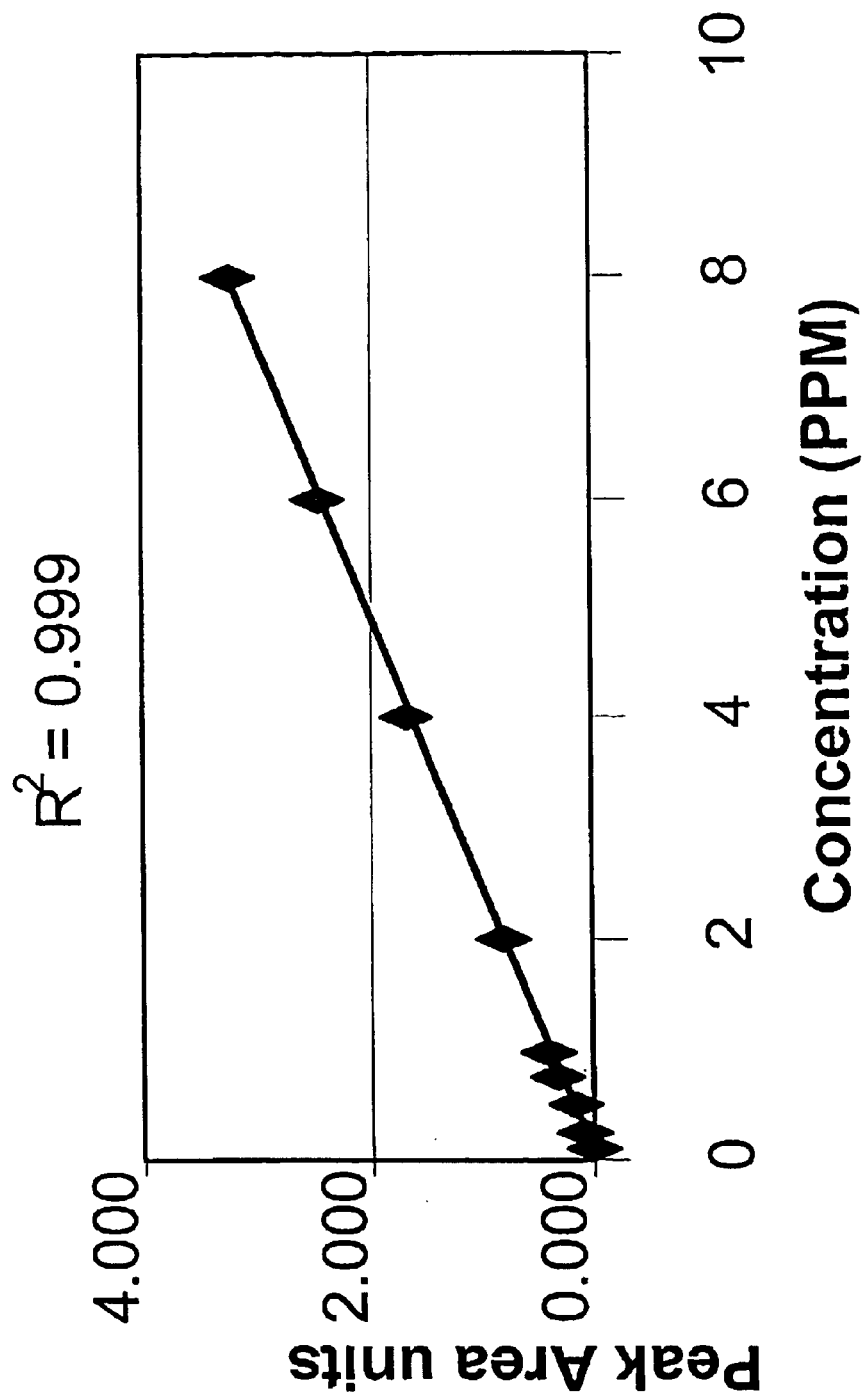

The experimental setup was similar to Example 7 with the exception that a number of standards between 0 and 8 ppm were injected. The response versus concentration curves showed excellent linearity for all the cations including ammonia in the above concentration range. Correlation coefficient of greater than 0.999 was achieved for all of the ions. Response versus concentration curve for ammonia is shown in FIG. 13.

What is claimed is:

1. A method for suppressed ion analysis of a plurality of different analyte ions in a sample solution, each of said analyte ions being of a common charge, positive or negative, said method comprising:

(a) eluting said sample solution with an eluent, comprising electrolyte counterions of opposite charge to said analyte ions, through a separating medium effective to separate said analyte ions to form a separating medium effluent stream, (b) flowing said separating medium effluent stream through a suppression zone in which electrolyte counterions are removed to convert said electrolyte to weakly ionized form to form a suppressor sample effluent stream, and (c) converting said analyte ions in said suppressor sample effluent stream into salts in a salt-forming zone by reaction with salt-forming ions of opposite charge comprising said removed electrolyte counterions to form an analyte salt stream.

2. The method of claim 1 further comprising the step of (d) detecting said analyte ions in salt form in said analyte salt stream.

3. The method of claim 1 in which step (b) is performed by flowing said separating medium effluent stream through a suppressor sample flow channel in said suppressor zone separated from a suppressor regenerant flow channel by a suppressor ion exchange membrane having exchangeable ions of opposite charge to said analyte ions, and flowing a regenerant stream through said suppressor regenerant flow channel, said electrolyte counterions being removed from said separating medium effluent stream by passing across said suppressor ion exchange membrane into said suppressor regenerant stream to form a suppressor regenerant effluent stream containing electrolyte counterions.

4. The method of claim 3 in which step (c) is performed by flowing said suppressor regenerant effluent stream through a salt converting zone remote from said suppression zone having a salt convertor regenerant flow channel separated by a salt convertor ion exchange membrane, having exchangeable ions of opposite charge to said analyte ions, from an analyte salt-forming flow channel, and flowing said suppressor sample flow stream through said analyte salt-forming flow channel, said electrolyte counterions passing from said salt convertor regenerant flow channel through said salt convertor ion exchange membrane from said regenerant effluent stream into said analyte salt-forming flow channel to form said analyte salt stream.

5. The method of claim 4 in which an electrical potential is applied across said salt convertor ion exchange membrane between a cathode communicating with said analyte salt-forming flow channel and an anode communicating with said salt convertor regenerant flow channel.

6. The method of claim 4 in which an electrical potential is applied across said salt convertor membrane between an anode communicating with said analyte salt-forming flow channel and a cathode communicating with said salt convertor regenerant flow channel.

7. The method of claim 4 further comprising the step of:
(d) detecting said analyte ions in salt form in salt analyte salt stream.

8. The method of claim 7 which after, detection in step (d), said analyte salt stream is recycled to said suppressor regenerant flow channel.

9. The method of claim 4 in which an electrical potential is applied across said salt convertor ion exchange membrane between first and second electrodes of opposite charge communicating with said salt convertor regenerant flow channel and said analyte salt-forming flow channel, respectively.

10. The method of claim 9 in which said analyte ions are of negative charge, said first electrode is an anode and said second electrode is a cathode.

11. The method of claim 9 in which said analyte ions are of positive charge, said first electrode is a cathode and said second electrode is an anode.

12. The method of claim 4 in which the streams in said analyte salt-forming flow channel and said salt convertor regenerant flow channel flow in the same direction.

13. The method of claim 3 in which said separating medium effluent stream in said suppressor sample flow channel and said suppressor regenerant stream in said suppressor regenerant flow channel flow in the same direction.

14. The method of claim 3 in which said salt-forming zone is coextensive with the outlet section of said suppressor ion exchange membrane which includes exchangeable ions in the form of said electrolyte counterions, a portion of which form salts with said sample analyte ions.

15. The method of claim 14 for the analysis of anion analytes in which an electrical potential is applied across said suppressor ion exchange membrane in said suppression zone between an anode communicating with said suppressor sample flow channel and a cathode communicating with said suppressor regenerant flow channel.

16. The method of claim 15 in which an electrical potential is applied across said suppressor ion exchange membrane in said salt-forming zone between a cathode communicating with said suppressor sample flow channel and an anode communicating with said regenerant flow channel.

17. The method of claim 15 in which an electrical potential is not applied across at least a portion of said salt-forming zone.

18. The method of claim 14 for the analysis of cation analytes in which an electrical potential is applied across said suppressor ion exchange membrane in said suppression zone between a cathode communicating with said suppressor sample flow channel and an anode communicating with said suppressor regenerant flow channel.

19. The method of claim 15 or 18 in which an electrical potential is applied across said suppressor ion exchange Membrane in said salt-forming zone between an anode communicating with said suppressor sample flow channel and a cathode communicating with said regenerant flow channel.

20. The method of claim 1 further comprising the step of:
(d) flowing said analyte salt stream through an acid or base convertor to form an effluent stream comprising acid of said electrolyte counterions for analyte ions of positive charge and a base of said electrolyte counterions for analyte ions of negative charge, and
(e) detecting said electrolyte counterions in said acid or base electrolyte counterion effluent stream.

21. The method of claim 20 in which step (d) is performed by flowing said analyte salt stream through a sample flow channel of said acid or base convertor separated by an acid or base convertor ion exchange membrane having exchangeable ions of the same charge as said analyte ions from an acid or base convertor, regenerant flow channel, and flowing an acid or base stream through said acid or base convertor regenerant flow channel.

22. The method of claim 21 in which, after detection in step (e), said acid or base electrolyte counterion effluent stream is recycled to said acid or base convertor regenerant flow channel.

23. The method of claim 1 in which said salt-forming zone comprises at least a first packed bed salt convertor including ion exchange medium with exchangeable electrolyte counterions.

24. The method of claim 23 in which said first packed bed salt convertor is periodically regenerated by a stream of said eluent electrolyte counterions that are removed from said suppression zone.

25. The method of claim 24 including a second packed bed salt convertor including ion exchange medium with exchangeable electrolyte counterions which are regenerated by a stream of said eluent electrolyte counterions that are removed from said suppression zone.

26. The method of claim 25 in which the flow to said first and second packed bed salt convertors is reversed so that said first packed bed salt convertor is being regenerated while said second one converts said analyte ions into an analyte salt stream.

27. A method for suppressed ion analysis of a plurality of analyte ions in a sample solution, each of said analyte ions being of a common charge, positive or negative, said method comprising:
(a) eluting said sample solution with an eluent, comprising electrolyte counterions of opposite charge to said analyte ions, through a separating medium effective to separate said analyte ions to form a separating medium effluent stream,
(b) flowing said separating medium effluent stream through a suppression zone in which said electrolyte counterions are removed to convert said electrolyte to weakly ionized form to form a suppression zone effluent stream comprising said analyte ions in acid or base form,
(c) converting said analyte ions in said suppression zone effluent stream into a salt in a first packed bed salt convertor including an ion exchange medium with exchangeable cations or anions by reaction with ions of opposite charge to said analyte ions comprising to form a first analyte salt stream,
(d) at the same time as step (c), regenerating an at least partially exhausted second packed bed salt convertor to salt-forming cations or anions,
(e) detecting said analyte ions in said first analyte salt stream, (f) reversing flow through the first and second packed bed salt convertors so that said first one is being regenerated while a second analyte salt stream is formed in said second packed bed salt convertor, and (g) detecting said analyte ions in said second analyte salt stream.

* * * * *